US006387639B1

(12) United States Patent
Posner et al.

(10) Patent No.: US 6,387,639 B1
(45) Date of Patent: May 14, 2002

(54) MA FAMILY POLYPEPTIDES AND ANTI-MA ANTIBODIES

(75) Inventors: Jerome B. Posner; Josep O. Dalmau; Myrna R. Rosenfeld, all of New York, NY (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 0 days.

(21) Appl. No.: 09/189,527

(22) Filed: Nov. 10, 1998

(51) Int. Cl.$^7$ .................. G01N 33/53; G01N 33/564; G01N 33/574; C07K 16/28; C07K 16/30
(52) U.S. Cl. .................. 435/7.23; 435/7.1; 435/7.2; 435/7.21; 436/64; 436/501; 436/503; 436/811; 436/815; 530/387.1; 424/130.1
(58) Field of Search .............. 424/130.1; 530/387.1; 435/7.1, 7.2, 7.21, 7.23; 436/64, 501, 503, 506, 811, 815

(56) References Cited

U.S. PATENT DOCUMENTS

| 5,603,934 A | 2/1997 | Posner et al. ............. 424/185.1 |
| 5,614,371 A | 3/1997 | Posner et al. ............. 435/7.23 |
| 5,668,013 A | 9/1997 | Posner et al. ............. 435/320.1 |
| 5,807,705 A | 9/1998 | Posner et al. ............. 435/69.1 |

OTHER PUBLICATIONS

Burgess et al "Possible Dissociation of the Heparin–binding and Mitogenic Acitivies of Heparin–binding Growth Factor–1 from Its Receptor–binding Activities by Site–directed Mutagenesis of a single Lysine Residue", Journal of Cellular biology, vol. 111, pp, 1990.*
Lazar et al, "Transforming Growth Factor Alpha: Mutation of Aspartic Acid 47 and Leuine 48 Results in Different Biological Activities", Molecular and Cellular Biology, vol. 8, pp. 1247–1252, 1988.*
Yoshimura et al, "Epitope recognized by an anti–neuronal autoantibody associated with paraneoplastic neurological syndrome are conserved between vertebrate", Society for Neuroscience, vol. 22, No. 1–3, p. 983, 1996.*
Voltz, R., et al., "CD8 + T Cells are Primarily Involved in the Pathogenesis of the Anti–HU Paraneoplastic syndrome." Abstract.
Gultekin, S.H., et al. "Characterization of a Novel Antineuronal Antibody (Anti–Ta) in the Serum of 6 Patients with Testicular Cancer and Paraneoplastic Limbic Encephalopathy." Abstract.
Dalmau, J., et al., "The novel antibody (anti–Ma) from patients with paraneoplastic brainstem and cerebellar dysfunction recognizes MM1, a protein expressed in brain and testis," *J. Neurol*, 245:355–356 (1998).
Voltz, R., et al., "Sera of patients with testicular cancer and paraneoplastic limbic/brainstem encephalitis harbor an antineuronal antibody (anti–Ta) that recognizes a novel neuronal protein," Abstract.

Moll, J.W.B., et al., "Anti–neuronal antibodies in paraneoplastic neurological disorders with small–cell lung carcinoma." *Clin. Neurol. Neurosurg.* 92–3:223–228 (1990).
Moll, J.W.B., et al., "Immune diagnosis of paraneoplastic neurological disease." *Clin. Neurol. Neurosurg.* 97:71–81 (1995).
Peterson, K., et al., "Paraneoplastic cerebellar degeneration. I. A clinical analysis of 55 anti–Yo antibody–positive patients." *Neurology* 42:1931–1937 (1992).
Posner, J.B. and Dalmau, J. "Paraneoplastic syndromes." *Curr. Opin. Immunol.* 9:723–729 (1997).
Stenger, S. and Modlin, R.L. "Cytotoxic T cell responses to intracellular pathogens." *Curr. Opin. Immunol.* 10:471–477 (1998).
Sakai, K., et al., "Isolation of a Complementary NA Clone Encoding an Autoantigen Recognized by an Anti–Neuronal Cell Antibiody from a Patient with Paraneoplastic Cerebellar Degeneration." *Ann. Neurol.* 28:692–698 (1990).
Sillevis–Smitt, P., et al. "Pitfalls in the diagnosis of autoantibodies associated with paraneoplastic neurologic disease." *Neurology*, 46:1739–1741 (1996).
Szabo, A., et al., HuD, a Paraneoplastic Encephalomyelitis Antigen, Contains RNA–Binding Domains and Is Homologous to Elav and Sex–lethal. *Cell* 67:325–333 (1981).
Fathallah–Shayk, H., et al., "Cloning of a leucine–zipper protein recognized by the sera of patients with antibody–associated paraneoplastic cerebellar degeneration." *Proc. Natl. Acad. Sci. USA.* 88:3451–3454 (1991).
Furneaux, H.M., et al., "Selective Expression of Purkinje–cell antigens in tumor tissue from patients with paraneoplastic cerebellar degeneration." *NEJM.* 322(26):1844–1851 (1990).
Furneaux, H.M., et al., "Antoantibody synthesis in the central nervous system of pateints with paraneoplastic syndromes." *Neurology* 40:1085–1091 (1990).
Graus, F., et al., "Neuronal antinuclear antibody in sensory neuropathy from lung cancer." *Neurology* 35:538–543 (1985).
Graus, F., et al., "Immunological characterization of a neuronal antibody (anti–Tr) asssociated with paraneoplastic cerebellar degeneration and Hodgkin's disease." *J. Neuroimmunology*. 74:55–61 (1997).

*Primary Examiner*—Anthony C. Caputa
*Assistant Examiner*—Karen A. Canella
(74) *Attorney, Agent, or Firm*—Hamilton, Brook, Smith & Reynolds, P.C.

(57) ABSTRACT

Ma family polypeptides Ma1, Ma2, Ma3, Ma4 and Ma5 are disclosed, as are nucleic acids encoding the Ma family polypeptides, antibodies that bind to Ma family polypeptides, and methods of diagnosis of paraneoplastic syndromes, by assessing a test sample from an individual for the presence or absence, or amount, of antibodies to Ma family polypeptides.

46 Claims, 18 Drawing Sheets

OTHER PUBLICATIONS

Luque, F.A., et al., "Anti–Ri: An Antibody Associated with Paraneoplastic Opsoclonus and Breast Cancer." *Ann. Neurol.* 29:241–251 (1991).

Moll, J.W.B., et al., "Diagnostic value of anti–neuronal antibodies for paraneoplastic disorders of the nervous system." *J. Neurol., Neuros, and Psychi.* 53:940–943 (1990).

Buckanovich, R.J., et al. "Nova, the Paraneoplastic Ri Antigen, Is Homologous to an RNA–Binding Protein and Is Specifically Expressed in the Developing Motor System", *Neuron.* 11:657–672 (1993).

Budde–Steffen, C., et al. "An Antineuronal Autoantibody in Paraneoplastic Opsoclonus", *Ann. Neurol.* 23:528–531 (1988).

Dalmau, J., et al. "Detection of the Anti–Hu Antibody in the Serum of Patients with Small Cell Lung Cancer—A Quantitative Western Blot Analysis", *Ann. Neurol.* 27:544–552 (1990).

Dalmau, J., et al., "Anti–Hu–Associated Paraneoplastic Encephalomyelitis/Sensory Neuronopathy", *Medicine* 71(2):59–72 (1992).

Dalmau, J.O. and Posner, J.B. "Paraneoplastic Syndromes Affecting the Nervous System," *Sem. in Onc.* 24(3):318–328 (1997).

Darnell, R.B. "Onconeural antigens and the paraneoplastic neurologic disorders: At the intersection of cancer, immunity, and the brain." *Proc. Natl. Acad. Sci. USA.* 93:4529–4536 (1996).

Dropcho, E.J., et al. "Cloning of a brain protein identified by autoantibodies from a pateint with paraneoplastic cerebellar degeneration." *Proc. Natl. Acad. Sci. USA.* 84:4552–4556 (1987).

Dropcho, E.J. "Neurologic paraneoplastic syndromes," *J. Neuro. Sci.* 153:264–278 (1998).

Dropcho, E.J. "Autoimmune Central Nervous system Paraneoplastic Disorders: Mechanisms, Diagnosis, and Therapeutic Options," *Ann. Neurol.* 37(S1):S102–S113 (1995).

Ahern, G.L., et al. "Paraneoplastic temporal lobe epilepsy with testicular neoplasm and atypical amnesia," *Neurology*, 44:1270–1274 (1994).

Anderson, N.D., et al. "Paraneoplastic Cerebellar Degeneration: Clinical–Immunological Correlations," *Ann. Neurol.* 24:559–567 (1988).

Burton, G.V., et al. "Paraneoplastic Limbic Encephalopathy With Testicular Carcinoma," *Cancer*, 62:2248–2251 (1988).

* cited by examiner

```
cgaggagcga cggccggacc cagacccaga cgcaagatgg cgacggccgc gtgactgcct         60
cagcgtcccc gagctcggct ccgagtgcac ctacggactg actgtggggg cagagaaggg        120
cgagatcagg actctgtctt tgttaatcgt gactgcatga aggtcgcctc cctcgggcct        180
acttggtggg agtgtctggt attgttctaa ggccaggagc acggtgagcc acagtctgtt        240
ggtagaattt ggcgtcttga tagttgagaa a atg gcg atg aca ctg ttg gaa          292
                                  Met Ala Met Thr Leu Glu
                                    1                  5 gac tgg tgc cgg ggg atg gat gtg aac tcc cag aga act ctg tta gtc         340
Asp Trp Cys Arg Gly Met Asp Val Asn Ser Gln Arg Thr Leu Leu Val
 10                              15                  20 tgg ggc atc cca gtg aac tgt gat gag gct gaa atc gaa gag acc ctc         388
Trp Gly Ile Pro Val Asn Cys Asp Glu Ala Glu Ile Glu Glu Thr Leu
         25                              30                  35 cag gct gcg atg ccc cag gtc tcc tac cga atg ctt ggg aga atg ttc         436
Gln Ala Ala Met Pro Gln Val Ser Tyr Arg Met Leu Gly Arg Met Phe
 40                              45                  50           55 tgg agg gaa gaa aat gcg gcg atc ccc gcc tta gag tta gag ctc act ggc gct 484
Trp Arg Glu Glu Asn Ala Ala Ile Pro Ala Leu Leu Glu Leu Thr Gly Ala
         60                              65                  70 gta gat tac gcc gcg gcg atc ttt aag ccc cca act gat gct gaa ttt tta gaa 532
Val Asp Tyr Ala Ala Ile Phe Lys Pro Pro Thr Asp Ala Glu Phe Leu Glu
 75                              80                  85 tgg aaa gtg tta ttt aag ccc gcg gag atg ccg ggc aaa gga ggg gtc         580
Trp Lys Val Leu Phe Lys Pro Arg Glu Met Pro Gly Lys Gly Gly Val
         90                              95                 100 aga ttg cac ctc ttc cta gct aga gag ggg tgg acc gtg caa gat gtt         628
Arg Leu His Leu Phe Leu Ala Arg Glu Gly Trp Thr Val Gln Asp Val
105                             110                 115
```

FIG. 1A

```
gcc cgt gtc ctt ggg ttt cag aac cct act ccg acc ccg ggc cca gag    676
Ala Arg Val Leu Gly Phe Gln Asn Pro Thr Pro Thr Pro Gly Pro Glu
120                 125                 130                 135 atg cca gca gag atg cta aac tat att ttg gat aat gtt att cag cct    724
Met Pro Ala Glu Met Leu Asn Tyr Ile Leu Asp Asn Val Ile Gln Pro
        140                 145                 150 ctt gtt gag tcc ata tgg tac aag agg ctg aca ctt ttc tcg ggg aag    772
Leu Val Glu Ser Ile Trp Tyr Lys Arg Leu Thr Leu Phe Ser Gly Lys
    155                 160                 165 gga cat ccc agg gcc tgg aga gga aac ttt gat ccc tgg ctg gag cac    820
Gly His Pro Arg Ala Trp Arg Gly Asn Phe Asp Pro Trp Leu Glu His
170                 175                 180 act aat gag gtc cta gag gag tgg cag gtg tcc gat gta gaa aag agg    868
Thr Asn Glu Val Leu Glu Glu Trp Gln Val Ser Asp Val Glu Lys Arg
        185                 190                 195 cgg cgg ttg atg gag agt ctt aga ggc ccc gcc gct gat gtt att cgc    916
Arg Arg Leu Met Glu Ser Leu Arg Gly Pro Ala Ala Asp Val Ile Arg
    200                 205                 210                 215 atc ctt aag tcc aac aac ccc gcg ata acc act gcc gaa tgc ctg aag    964
Ile Leu Lys Ser Asn Asn Pro Ala Ile Thr Thr Ala Glu Cys Leu Lys
220                 225                 230 gcg ctt gag cag gtg ttt ggg agc gtt gag agc tct agg gat gcc cag    1012
Ala Leu Glu Gln Val Phe Gly Ser Val Glu Ser Ser Arg Asp Ala Gln
        235                 240                 245
```

FIG. 1B

```
atc aaa ttt ctg aac act tat cag aac ccg gga gaa aaa ttg tct gct    1060
Ile Lys Phe Leu Asn Thr Tyr Gln Asn Pro Gly Glu Lys Leu Ser Ala
             250                 255                 260 tat gtc att cgt ctg gag cct ctg cta cag aag gtg gta gag aag ggg    1108
Tyr Val Ile Arg Leu Glu Pro Leu Leu Gln Lys Val Val Glu Lys Gly
         265                 270                 275 gcc att gat aaa gat aat gtg aac cag gcc cgc cta gag cag gtc att    1156
Ala Ile Asp Lys Asp Asn Val Asn Gln Ala Arg Leu Glu Gln Val Ile
     280                 285                 290                295 gcc ggg gcc aac cac agc ggg gcc atc cga agg cag ctg tgg ctt acc    1204
Ala Gly Ala Asn His Ser Gly Ala Ile Arg Arg Gln Leu Trp Leu Thr
                 300                 305                 310 ggg gct ggg gaa ggg cca ggc ccc aaa cct ctt tca gtt gct ggt gca    1252
Gly Ala Gly Glu Gly Pro Gly Pro Lys Pro Leu Ser Val Ala Gly Ala
             315                 320                 325 gat ccg tgaggaggaa gcccaggag gaggaggag aggctgaggc caccctttctg      1308
Asp Pro cagttaggcc tggaagggca cttctgagtg ccaggaaagg cagctttagt gcagacctag  1368
atcacagcta ctttcttgt ccctgtgggg tcttacagat gtgtctctga gtagtaaagg   1428
cttagcctg ttctgttttg ttgttttg gagggaagg accgtgaacg ttagtcaggc ctgagtattc 1488
atgtaacatt ctaaaattgt gccagcgagc aatgggttg gttggacaca gcgcttagtg aagcgggtct 1548
tgctggctaa aatgcccagg taaaggggtg tgtgaaaaac acgcgaacct atgacacttc cacgctgtca 1608
tcatgacat cataatcagt tcagatgttt nactacgagg cctggctcac ttattccaca             1668
ctgaatgtga aattgcatgt agattactga taacgcggat agattttgt aggaagtgtt             1728
cagtaaaagt tttatattaa tggaaggaag tgtgcattta acatgtcgac cagttaatt             1788
ttgttccaga atcttattc tcatcttaa acatgtcgac cagttaatt gaaaagtatt              1848
caatgcaaac aaaatgggt gttaaaaaat actgcagtta cggagctgtg taaaccagtt             1908
ctgagactgc aaaatgggt gttaaaaatt actgcagtta cggagctgtg taaaccagtt             1968
tctcattgca taagatacag atgtaaattg catggagagg ttgatatgca cctgtacagt            2028
aattcactcc cccatttcac ttctttgtca gagaatagtt cttgttcata ctgagtgttc            2088
taaatttgaa gttatatata caaattaaaa tattttaaaa aaaaaaaaaa g                     2139
```

FIG. 1C

```
ccc ctg gca ctg tta gag gac tgg tgc agg ata atg agt gtg gat gag      48
Pro Leu Ala Leu Leu Glu Asp Trp Cys Arg Ile Met Ser Val Asp Glu
 1               5                  10                  15 cag aag tca ctg atg gtt acg ggg ata ccg gcg gac ttt gag gag gct      96
Gln Lys Ser Leu Met Val Thr Gly Ile Pro Ala Asp Phe Glu Glu Ala
             20                  25                  30 gag att cag gag gtc ctt cag gag act tta aag tct ctg ggc agg tat     144
Glu Ile Gln Glu Val Leu Gln Glu Thr Leu Lys Ser Leu Gly Arg Tyr
         35                  40                  45 aga ctg ctt ggc aag ata ttc cgg aag cag gag aat gcc aat gct gtc     192
Arg Leu Leu Gly Lys Ile Phe Arg Lys Gln Glu Asn Ala Asn Ala Val
     50                  55                  60 tta cta gag ctt ctg gaa gat act gat gtc tcg gcc att ccc agt gag     240
Leu Leu Glu Leu Leu Glu Asp Thr Asp Val Ser Ala Ile Pro Ser Glu
 65                  70                  75                  80 gtc cag gga aag ggg ggt gtc tgg aaa gtg atc ttt aag acc cct aat     288
Val Gln Gly Lys Gly Gly Val Trp Lys Val Ile Phe Lys Thr Pro Asn
                 85                  90                  95
```

FIG. 2A

```
cag gac act gag ttt ctt gaa aga ttg aac ctg ttt cta gaa aaa gag    336
Gln Asp Thr Glu Phe Leu Glu Arg Leu Asn Leu Phe Leu Glu Lys Glu
            100                 105                 110 ggg cag acg gtc tcg ggt atg ttt cga gcc ctg ggg cag gag gcg ttg    384
Gly Gln Thr Val Ser Gly Met Phe Arg Ala Leu Gly Gln Glu Ala Leu
        115                 120                 125 tct cca gcc aca gtg ccc tgc atc tca cca gaa tta ctg gcc cat ttg    432
Ser Pro Ala Thr Val Pro Cys Ile Ser Pro Glu Leu Leu Ala His Leu
    130                 135                 140 ttg gga cag gca atg gca cat gcg cct cag ccc ctg cta ccc atg aga    480
Leu Gly Gln Ala Met Ala His Ala Pro Gln Pro Leu Leu Pro Met Arg
145                 150                 155                 160 tac cgg aaa ctg cga gta ttc tca ggg agt gct gtc cca gcc cca gag    528
Tyr Arg Lys Leu Arg Val Phe Ser Gly Ser Ala Val Pro Ala Pro Glu
            165                 170                 175 gaa gag tcc ttt gag gtc tgg ttg gaa cag gcc acg gag ata gtc aaa    576
Glu Glu Ser Phe Glu Val Trp Leu Glu Gln Ala Thr Glu Ile Val Lys
        180                 185                 190 gag tgg cct tgaacacaac caaaaaaaaa aaaaaaaaag                        615
Glu Trp Pro
        195
```

```
Ma2   .TAGAAAAAGAGGGGCAGACGGTCTCGG.GTATGTTTCGAGCCCTGGGGCAGGAGGCGTTGTCTCCAGCCACAGTGCCCTGC.AT    407
         ||| ||||||||||||||| ||||||| ||||| ||| ||||| ||||||||||||| || |||| ||||  ||||||| ||
Ma1   .TAGctAgAGAGGGGtgACCgTgcaaG.aTgTtgccCgTgtcCgttcAGaacoctaCTCCgaCCcC..GggCCCaGaGaAT      1071
                                          |||||||  || |||| |    ||| ||| |||| ||| |||
mouse tTAGgggAAcA.....CAGAcTgCtgCTTgGGaGgATGTT.........CAGGAGG.GaTGagaaCAagaAtgtaGCCCTG....   374

Ma2   CTCACCAGAATTACTGGCCCATTTGTTGGGACAGGCAATGGCACATGCGCCTCAGCCCCTGCTAC...CCATG.AGATACCGGAA       488
      ||  ||||||| | ||||||  ||||| |||| |||  |||| |||| |||||||| |          ||||  |||||| |||
Ma1   gcCAgCAGAgaTgCTaaacTaTaTtTTGGataAtGttAT..........TCAGCCctCTtgTtgagtCCATa.tGGTACaaGAg      1143
                                                              |||||  |       |||| |||||| ||
mouse ..........AtTGGgCTtacagTaGaGACTgGCAgTG.........................CCTGgTcC...CCAaGAaATACCtGcA 427

Ma2   ACTGCGAGTATTCTCAGGGA.GTGCTGTCCCAGCCCC...AGAGGAAGAGTC.CTTTGAGGTCTCGTTGGAACAGGCCACGGAGA       568
       ||| |||| |  | |||   ||  |  || || ||||   |||      |  || ||    ||| ||  | |||  |  ||||
Ma1   gCTGacAcTtTTTCTCgGGGAaGgGacaTCCCAGggCCtggAGAGAGGAAa......CTTTGAtccCTGGCTGGAgCAcacTAatGAGg   1223
                                                                ||      |     |||     || |||
mouse AaaG.GAGgtgTCTg.GaGA.GTGaTcTTttaAGCCtCctgAtActgAtAGTgacTTTTtGtgCaGaTTaaAtgAG......         499

Ma2   TAGTCAAAGAGTGGCCTTGAACACAACCAAAAAAAAAAAAAG                                              615
       ||  | || |||  |     | |  ||   |||
Ma1   TccTagAgGAGTGGC.....AggtgtCCgA>                                                         1248
         || |||||| |
mouse TttTtAAAGgGgG....aGggCAtgACGAtgggtgAAtt>                                                534
```

FIG. 3B

```
  g gac ctc atg cac ata gtg cag gca gac aac ccg tcc atc agt gta gaa    49
    Asp Leu Met His Ile Val Gln Ala Asp Asn Pro Ser Ile Ser Val Glu
     1               5                  10                  15 gag tgt ttg gag gcc ttt aag caa gtg ttt ggg agc cta gag agc cgc        97
Glu Cys Leu Glu Ala Phe Lys Gln Val Phe Gly Ser Leu Glu Ser Arg
                    20                  25                  30 agg aca gcc cag gtg agg tat ctg aag ccc tat cag gag gaa gga gag       145
Arg Thr Ala Gln Val Arg Tyr Leu Lys Pro Tyr Gln Glu Glu Gly Glu
                35                  40                  45 aag gtc tca gcc tat gtg tta cgg cta gaa acc ctg ctc cgg aga gcg       193
Lys Val Ser Ala Tyr Val Leu Arg Leu Glu Thr Leu Leu Arg Arg Ala
            50                  55                  60 gtg gag aaa cgc gcc atc cct cgg cgt att gcg gac cag gtc cgc ctg       241
Val Glu Lys Arg Ala Ile Pro Arg Arg Ile Ala Asp Gln Val Arg Leu
        65                  70                  75              80
```

FIG. 5A

```
gag cag gtc atg gct ggg gcc act ctt aac cag atg ctg tgg tgc cgg      289
Glu Gln Val Met Ala Gly Ala Thr Leu Asn Gln Met Leu Trp Cys Arg
                 85                  90                  95 ctt agg gag ctg aag gat cag ggc ccg ccc ccc agc ttc ctt gag cta      337
Leu Arg Glu Leu Lys Asp Gln Gly Pro Pro Pro Ser Phe Leu Glu Leu
            100                 105                 110 atg aag gta ata cgg gaa gag gaa gag gcc tcc ttt gag aat              385
Met Lys Val Ile Arg Glu Glu Glu Glu Ala Ser Phe Glu Asn
            115                 120                 125 gag agt atc gaa gag cca gag gaa cga gat ggc tat ggc cgc tgg aat      433
Glu Ser Ile Glu Glu Pro Glu Glu Arg Asp Gly Tyr Gly Arg Trp Asn
            130                 135                 140 cat gag gga gac gac tgaaaaccac ctgggggcag gacccacagc cagtgggcta      488
His Glu Gly Asp Asp
145 agacctttaa aaaatttttt tctttaatgt atgggactga aatcaaaacca tgaaagccaa   548
ttattgacct tcctccttc cttcctccc tcctctctc cttctctcct tctctccttt       608
tttttttttt ttttaaacc ctgtccttgg gtgggtgtgg gtataatact aagttgagat     668
gatatcattt acggggaag gcgctttgtg aagtaggcct tatttctctt gtccttcgt      728
acagggagga atttgaagta gatagaaacc gacctgatt actccggtct gaactcagat     788
cacgtaggac tttaatcgtt gaacaaacga acctttaata gcggg                    833
```

FIG. 5B

```
g gtc cag gga aag ggg ggt gtc tgg aag gtg atc ttt aag acc cct aat     49
  Val Gln Gly Lys Gly Gly Val Trp Lys Val Ile Phe Lys Thr Pro Asn
   1               5                  10                  15 cag gac act gag ttt ctt gaa aga ttg aac ctg ttt cta gaa aaa gag       97
Gln Asp Thr Glu Phe Leu Glu Arg Leu Asn Leu Phe Leu Glu Lys Glu
         20                  25                  30 ggg cag acg gtc tcg ggt atg ttt cga gcc ctg ggg cag gag ggc gtg      145
Gly Gln Thr Val Ser Gly Met Phe Arg Ala Leu Gly Gln Glu Gly Val
     35                  40                  45 tct cca gcc aca gtg ccc atc tgc tca cca gaa tta ctg gcc cat ttg      193
Ser Pro Ala Thr Val Pro Cys Ile Ser Pro Glu Leu Leu Ala His Leu
 50                  55                  60 ttg gga cag gca atg gca cat gcg cct cag ccc ctg cta ccc atg aga      241
Leu Gly Gln Ala Met Ala His Ala Pro Gln Pro Leu Leu Pro Met Arg
 65                  70                  75                  80 tac cgg aaa ctg cga gta ttc tca ggg agt gct gtc cca gcc cca gag      289
Tyr Arg Lys Leu Arg Val Phe Ser Gly Ser Ala Val Pro Ala Pro Glu
                 85                  90                  95
```

FIG. 6A

```
gaa gag tcc ttt gag gtc tgg ttg gaa cag gcc acg gag ata gtc aaa    337
Glu Glu Ser Phe Glu Val Trp Leu Glu Gln Ala Thr Glu Ile Val Lys
            100                 105                 110 gag tgg cca gta aca gag gca gaa gag gca aag aaa agg tgg ctg gcg gaa agc    385
Glu Trp Pro Val Thr Glu Ala Glu Glu Ala Lys Lys Arg Trp Leu Ala Glu Ser
            115                 120                 125 ctg cgg ggc cct gcc ctg gac ctc atg cac ata gtg cag gca gac aac    433
Leu Arg Gly Pro Ala Leu Asp Leu Met His Ile Val Gln Ala Asp Asn
            130                 135                 140 ccg atc agt gta gaa gag tgt ttg gag gcc ttt aag caa gtg ttt    481
Pro Ile Ser Val Glu Glu Cys Leu Glu Ala Phe Lys Gln Val Phe
            145                 150                 155                 160 ggg agc cta gag agc cgc agg aca gcc cag gtg agg tat ctg aag acc    529
Gly Ser Leu Glu Ser Arg Arg Thr Ala Gln Val Arg Tyr Leu Lys Thr
            165                 170                 175 tat cag gag gaa gga gag gag aag gtc tca gcc tat gtg tta cgg cta gaa    577
Tyr Gln Glu Glu Gly Glu Glu Lys Val Ser Ala Tyr Val Leu Arg Leu Glu
            180                 185                 190
```

FIG. 6B

```
acc ctg ctc cgg aaa gcg gtg gag aaa cgc gcc atc cct cgg cgt att    625
Thr Leu Leu Arg Lys Ala Val Glu Lys Arg Ala Ile Pro Arg Arg Ile
                195                 200                 205 gcg gac cag gtc cgc ctg gag cag gtc atg gct ggg gcc act ctt aac    673
Ala Asp Gln Val Arg Leu Glu Gln Val Met Ala Gly Ala Thr Leu Asn
            210                 215                 220 cag atg ctg tgg tgc cgg ctt agg gag ctg aag gat cag ggc ccg ccc    721
Gln Met Leu Trp Cys Arg Leu Arg Glu Leu Lys Asp Gln Gly Pro Pro
        225                 230                 235                 240 ccc agc ttc ctt gag cta atg aag gta ata cgg gaa gag gag gag gaa    769
Pro Ser Phe Leu Glu Leu Met Lys Val Ile Arg Glu Glu Glu Glu Glu
                245                 250                 255 gag gcc tcc ttt gag aat cat gag agt atc gaa gag cca gag gaa cga gat    817
Glu Ala Ser Phe Glu Asn His Glu Ser Ile Glu Glu Pro Glu Glu Arg Asp
            260                 265                 270 ggc tat ggc cgc tgg aat cat gag gga gac gac tgaaaaccac ctgggggcag    870
Gly Tyr Gly Arg Trp Asn His Glu Gly Asp Asp
        275                 280 gacccacagc cagtgggcta agacctttaa aaaattttttt tctttaatgt atgggactga    930
aatcaaacca tgaaagccaa ttattgacct tcctcctc tcctcctcc ttcccttcct      990
cctctctcc ttctctcctc ctctctcctc ctttattct tgggtctcac tctcatcacc ctccttcct  1050
tttttctttt tctcttttct caaaaatctc ggctcactgc agccttgact tccaggctc caggctagag  1110
tgcagtggca caaaagcca ccttagcctc cccagtacct gggactacag gtttgctgt aggctcaggt  1170
gatcctcaca ccttagcctc gtatttttgg tagagacagg gtttgctgt gcacgcacca ccatgcctag  1230
ctattcttt gtatttttgg tagagacagg gtttgctgt gttgctcagg ctggtctgga  1290
accctaggc tcaaatgatg tgcccaactc ggcctcccaa agtgctggga ttacaggcat  1350
gaaccgccat gcctgccct tgatttttct ttttaagaaa aaaatatcta ggagtttctt  1410
agaccctatg tagattatta atgaacaaaa gattaaactc caaatactc aaatattaa  1470
tgaaggaatc tgaaacactt gtacttccaa ttttctttaa ataatcccaa atagaccaga  1530
attggcccat accatagaag aaagaattgg cagtcaaaaa aaaa                   1574
```

FIG. 6C cattagtatc cgcagagatt cgaggac atg ccg ttg acc ttg tta cag gac tgg    54
                        Met Pro Leu Thr Leu Leu Gln Asp Trp
                         1               5 tgt cgg ggg gaa cac ctg aac acc cgg agg tgc atg ctc atc ctg ggg     102
Cys Arg Gly Glu His Leu Asn Thr Arg Arg Cys Met Leu Ile Leu Gly
         10                  15                  20             25 atc ccc gag gac tgt ggc gag gat gag ttt gag gag aca ctc cag gag     150
Ile Pro Glu Asp Cys Gly Glu Asp Glu Phe Glu Glu Thr Leu Gln Glu
             30                  35                  40 gct tgc agg cac ctg ggc aga tac agg gtg att ggc agg atg ttt agg     198
Ala Cys Arg His Leu Gly Arg Tyr Arg Val Ile Gly Arg Met Phe Arg
                 45                  50                  55 agg gag gag aac gcc cag gcg att cta ctg gag ctg gca caa gat atc     246
Arg Glu Glu Asn Ala Gln Ala Ile Leu Leu Glu Leu Ala Gln Asp Ile
                     60                  65                  70

FIG. 7A

```
gac tat gct ttg ctc cca agg gaa ata cca gga aag ggg ccc tgg    294
Asp Tyr Ala Leu Leu Pro Arg Glu Ile Pro Gly Lys Gly Pro Trp
         75                  80                  85 gaa gtg att gta aaa ccc cgt aac tca gat ggg gaa ttt ctc aac aga    342
Glu Val Ile Val Lys Pro Arg Asn Ser Asp Gly Glu Phe Leu Asn Arg
         90                  95                 100             105 ctg aac cgc ttc tta gag gag agg cgg acc gtg tca gat atg aac        390
Leu Asn Arg Phe Leu Glu Glu Arg Arg Thr Val Ser Asp Met Asn
                110                 115                 120 cga gtc ctc ggg tcg gac acc aat tgt tcg gct cca aga gtg act ata    438
Arg Val Leu Gly Ser Asp Thr Asn Cys Ser Ala Pro Arg Val Thr Ile
        125                 130                 135 tca cca gag ttc tgg acc tgg gcc cag act ctg ggg gca gca gtg cag    486
Ser Pro Glu Phe Trp Thr Trp Ala Gln Thr Leu Gly Ala Ala Val Gln
        140                 145                 150 cct cta gaa caa atg ttg tac cga gaa cta aga gtg ttt tct ggg        534
Pro Leu Glu Gln Met Leu Tyr Arg Glu Leu Arg Val Phe Ser Gly
        155                 160                 165 aac acc ata tcc atc cca ggt gca ctg gcc ttt gat gcc tgg ctt gag    582
Asn Thr Ile Ser Ile Pro Gly Ala Leu Ala Phe Asp Ala Trp Leu Glu
        170                 175                 180             185
```

FIG. 7B

```
cac acc act gag atg cta cag atg tgg cag gtg ccc gag ggg gaa aag      630
His Thr Thr Glu Met Leu Gln Met Trp Gln Val Pro Glu Gly Glu Lys
            190                 195                 200 agg cgg agg ctg atg gaa tgc tta cgg ggc cct gct ctc cag gtc gtc      678
Arg Arg Arg Leu Met Glu Cys Leu Arg Gly Pro Ala Leu Gln Val Val
        205                 210                 215 agt ggg ctc cgg gcc agc aat gct tcc ata act gtg gag gag tgc ctg      726
Ser Gly Leu Arg Ala Ser Asn Ala Ser Ile Thr Val Glu Glu Cys Leu
    220                 225                 230 gct gcc ttg cag cag gtg ttc gga cct gtg gag agc cat aaa att gcc      774
Ala Ala Leu Gln Gln Val Phe Gly Pro Val Glu Ser His Lys Ile Ala
235                 240                 245 cag gtg aag ttg tgt aaa tgt aaa ttg tgt gcc tat cag gag gca gga gag aaa gta tct      822
Gln Val Lys Leu Cys Lys Ala Tyr Gln Glu Ala Gly Glu Lys Val Ser
        250                 255                 260                 265 agc ttt gtg tta cgt ttg gaa ccc ctg ctc caa aga gct gta gaa aac      870
Ser Phe Val Leu Arg Leu Glu Pro Leu Leu Gln Arg Ala Val Glu Asn
        270                 275                 280 aat gtg gta tca cgt aga aac gtg aat cag act cgc ctg aaa cga gtc      918
Asn Val Val Ser Arg Arg Asn Val Asn Gln Thr Arg Leu Lys Arg Val
    285                 290                 295 tta agt ggg gcc acc ctt cct gac aaa ctc cga gat aag ctt aag ctg      966
```

FIG. 7C

```
Leu Ser Gly Ala Thr Leu Pro Asp Lys Leu Arg Asp Lys Leu Lys Leu
            300                 305                 310 atg aaa cag cga agg aag cct cct ggt ttc ctg gcc ctg gtg aag ctc    1014
Met Lys Gln Arg Arg Lys Pro Pro Gly Phe Leu Ala Leu Val Lys Leu
        315                 320                 325 ctg cgt gag gag gag gaa tgg gag gcc act tta ggt cca gat agg gag    1062
Leu Arg Glu Glu Glu Glu Trp Glu Ala Thr Leu Gly Pro Asp Arg Glu
330                 335                 340                 345 agt ctg gag ggg ctg gaa gta gcc cca cct gcc agg atc act            1110
Ser Leu Glu Gly Leu Glu Val Ala Pro Pro Ala Arg Ile Thr
                350                 355                 360 ggg gtt ggg gca gta cct ctc cct gcc tct ggc aac agt ttt gat gcg    1158
Gly Val Gly Ala Val Pro Leu Pro Ala Ser Gly Asn Ser Phe Asp Ala
            365                 370                 375 agg cct tcc cag ggc tac cgg cgc cgg agg ggc aga ggc caa cac cga    1206
Arg Pro Ser Gln Gly Tyr Arg Arg Arg Arg Gly Arg Gly Gln His Arg
        380                 385                 390 agg ggt ggt gtg gca agg gct ggc tct cga gga tca aga aaa cgg aaa    1254
Arg Gly Gly Val Ala Arg Ala Gly Ser Arg Gly Ser Arg Lys Arg Lys
    395                 400                 405 cgc cac aca ttc tgc tat agc tgt ggg gaa gac ggc cac atc agg gta    1302
Arg His Thr Phe Cys Tyr Ser Cys Gly Glu Asp Gly His Ile Arg Val
410                 415                 420                 425
```

FIG. 7D

```
cag tgc atc aac ccc tcc aac ctg ctc ttg gta aag cag aag aaa cag        1350
Gln Cys Ile Asn Pro Ser Asn Leu Leu Leu Val Lys Gln Lys Lys Gln
             430                 435                 440 gct gca gtt gag tcg gga aac ggg aac tgg gct tgg gac aag agc cat        1398
Ala Ala Val Glu Ser Gly Asn Gly Asn Trp Ala Trp Asp Lys Ser His
             445                 450                 455 ccc aag tcc aag gcc aag taggctcggg agaacagggc aacattcct                1446
Pro Lys Ser Lys Ala Lys
             460 accacagccc aaggagacaa aagagatatt gggaggaggg gaaagagaag cccagacaaa      1506
cagcagatga gttgagtggg gcagagggac agggcagcca gaccaaggcc aagcnttctc      1566
acccttnggc cagttgaaag ggactttcag caaccaagac cacctggcaa caggctcagt      1626
gggggtcagg tccaggtccc cgaagaggtg ctggagagga aagcaggggag ccactgcatc     1686
cagcacatgg ggtgcctggg cctcagatgg ggacccaaa gaagcagaag ctgaagaagg       1746
tacggctggg ggttctgtcc tgctcatcca accacccta aataccacc ctgtggactt        1806
tgagctgaac atgcccactg gccccccagg cacatgggac ctggaggagc ctacctgggg      1866
cctgcccctg ccagcaggtg ccagggctgg tgaggaagag ctggggggca gaggtaaagc      1926
cctgcaggg aggccacagg gtccatcccg tcttcaggat catctacact gcactagggg      1986
agccccagga agcagcacc ctggaggccc tgtgccagtg aggacaggag accctaaggc      2046
cccggagcc cagtgccagc cagagttgt gcaggcaagg agacaaaga ttgatgagaa        2106
gaccccagc aggggtactg ggtaccccggc aggccagtgc cctcacagtt gacttggacc      2166
agggctg tgaaggaaag tctttgttgc aaaggaggag gaaaagggag gacttggtag        2226
ggttttgtt cttctgcttg gg                                                2248
```

MA FAMILY POLYPEPTIDES AND ANTI-MA ANTIBODIES

GOVERNMENT SUPPORT

The invention was supported, in whole or in part, by grant NS-26064 from the National Institutes of health, and grant 08748 from the National Cancer Institute. The United States Government has certain rights in the invention.

BACKGROUND OF THE INVENTION

The concurrent existence of cancer with specific neurologic disorders, known as paraneoplastic syndromes, often requires extensive or invasive studies or is established at autopsy. Paraneoplastic symptoms usually precede the detection of the cancer, may affect any part of the nervous system, and are often more debilitating than the cancer itself. Paraneoplastic limbic encephalitis (PLE) is one of these syndromes, initially recognized in 1968 (Corsellis, J. A. N. et al., *Brain* 91:481–496 (1968)). The presenting symptoms of PLE are irritability, depression, seizures, severe memory deficit and dementia. These symptoms correlate with the areas of the nervous system with major pathological involvement (hippocampus, amygdala, hypothalamus, and insular and cingulate cortices) but most studies also show brainstem encephalitis (BE) and abnormalities in other areas that may or may not be clinically silent (Bakheit, A. M. O. et al, *J. Neurol. Neurosurg. Psychiatry* 53:1084–1088 (1990); Henson, R. A. and Urich, H., *Cancer and the Nervous System*, Blackwell Scientific Publications, Oxford, USA, 1989, pp. 314–345).

Due to the diversity of clinical symptoms and the frequent absence of specific markers, PLE is likely underdiagnosed. In patients with known cancer, symptoms of PLE can be attributed to other complications, including metastases to the brain, toxic and metabolic encephalopathy, infections, and side effects of cancer therapy. In about 60% of the patients, PLE precedes the detection of the tumor, complicating even more its clinical recognition (Dalmau, J. et al, *Medicine* 71:59–72 (1992); Alamowitch, S. et al., *Brain* 120:923–928 (1997)). The finding of abnormalities involving the mesial temporal lobes on MRI studies may raise the suspicion of PLE, but does not establish the diagnosis.

Some paraneoplastic syndromes affecting the nervous system are associated with antibodies that react with neuronal proteins and the causal tumor (onconeuronal antigens) (Greenlee, J. E. ,*Ann. Neurol* 12:102 (1982); Graus, F. et al., *Neurology* 35:538–543 (1985); Budde-Steffen, C. et al., *Ann. Neurol.* 23:528–531 (1988); Dalmau, J., and Posner, J. B., *Semin. Oncol.* 24:318–328 (1997)). Several of these antibodies are markers of specific neurologic syndromes associated with distinct types of cancer (Furneaux, H. M. et al., *New Engl. J. Med.* 322:1844–1851 (1990); Luque, F. A. et al., *Ann. Neurol.* 29:241–251 (1991); Dalmau, J. et al., *Medicine* 71:59–72 (1992)). The presence of some antibodies is so specific that disorders previously identified by brain biopsy, or at autopsy, can now be diagnosed serologically (Henson, R. A. et al., *Brain* 88:449–464 (1965); Anderson, N. E. et al., *Ann. Neurol.* 24:559–567 (1988); Dalnau, J. et al., *Ann. Neurol.* 27:544–552 (1990); Posner, J. B. (ed.), *Paraneoplastic Syndromes. Neurologic Complications of Cancer*, Philadelphia, FA Davis Company, pp. 353–385 (1995)). The expression of neuronal proteins by the tumor is probably a crucial step that breaks immune tolerance for otherwise normal neuronal proteins (Carpentier et al. *Neurology* 50:A354–355 (1998)).

To date, characteristic antineuronal antibodies have been discovered in only a few paraneoplastic disorders. Because of debilitating nature of paraneoplastic syndromes, as well as the diversity of clinical symptoms and the frequent absence of specific markers, it is critical to identify new means for diagnosing paraneoplastic syndromes.

SUMMARY OF THE INVENTION

The current invention pertains to isolated Ma family proteins, particularly Ma1 (SEQ ID NO:4), Ma2 (SEQ ID NO:7), Ma3 (SEQ ID NO:9), Ma4 (SEQ ID NO:11) and Ma5 (SEQ ID NO:13), as well as active or functional derivatives or fragments of the Ma family polypeptides. The invention also pertains to nucleic acids encoding Ma family polypeptides, as well as nucleic acid constructs comprising the nucleic acid molecules described herein operatively linked to a regulatory sequence, and to recombinant host cells comprising the nucleic acid molecules described herein operatively linked to a regulatory sequence. The invention also pertains to isolated antibodies, or antigen-binding fragments thereof, which selectively bind to Ma family polypeptides or active derivatives or fragments thereof.

The invention further pertains to methods of diagnosing a paraneoplastic syndrome in an individual, by assessing a test sample (e.g., of bodily fluid or tissue, or of antibodies isolated from a bodily fluid or tissue), for the presence, absence, or amount of antibodies that bind to a Ma family polypeptide such as Ma1 and/or Ma2. The presence of antibodies that bind to a Ma family polypeptide is indicative of the presence of a paraneoplastic syndrome; the absence of antibodies that bind to a Ma family polypeptide is indicative of the absence of a paraneoplastic syndrome. The invention additionally pertains to methods of diagnosing a neoplasm in an individual, by assessing a test sample (e.g., of bodily fluid or tissue, or of antibodies isolated from a bodily fluid or tissue), for the presence, absence, or amount of antibodies that bind to a Ma family polypeptide such as Ma1 and/or Ma2. The presence of antibodies that bind to a Ma family polypeptide is indicative of the presence of a neoplasm; the absence of antibodies that bind to a Ma family polypeptide is indicative of the absence of a neoplasm.

BRIEF DESCRIPTION OF THE DRAWINGS

FIGS. 1A–1C depict the cDNA (SEQ ID NO:3) and putative amino acid sequence (SEQ ID NO:4) for Ma1.

FIGS. 2A–2B depict the cDNA (SEQ ID NO:6) and putative amino acid sequence (SEQ ID NO:7) for Ma2.

FIGS. 3A–3B depict the homology between Ma1 cDNA (SEQ ID NO:3) and Ma2 cDNA (SEQ ID NO:6) and mouse cDNA (SEQ ID NO:14).

FIGS. 5A–5B depict the cDNA (SEQ ID NO:8) and putative amino acid sequence (SEQ ID NO:9) for Ma3.

FIGS. 6A–6C depict cDNA (SEQ ID NO:10) and putative amino acid sequence (SEQ ID NO:11) for Ma4.

FIGS. 7A–7E depict cDNA (SEQ ID NO:12) and putative amino acid sequence (SEQ ID NO:13) for Ma5.

DETAILED DESCRIPTION OF THE INVENTION

Figure 4:
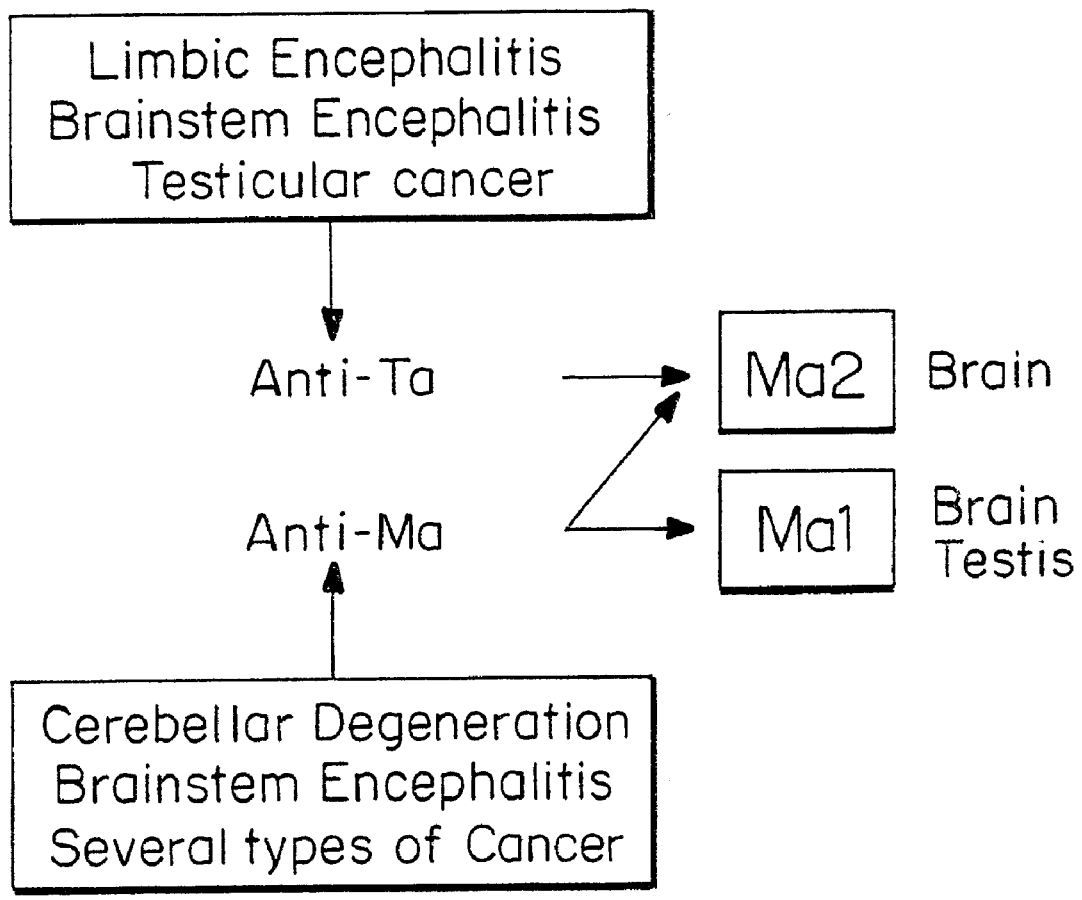
FIG. 4 depicts a summary of the clinical-inmmunological associations of antibodies to Ma1 and Ma2 to paraneoplastic syndromes.

The present invention relates to Ma family proteins, nucleic acids that encode Ma family proteins, and the relationship of the proteins to paraneoplastic syndromes. As described herein, Applicants have identified five proteins, Ma1, Ma2, Ma3, Ma4 and Ma5, and nucleic acids encoding them. Ma1 is a 37 kilodalton protein that is expressed in brain and testis; the presence of antibodies to Ma1 (also referred to herein as "anti-Ma antibodies") is associated with paraneoplastic syndromes, particularly those affecting the brainstem or cerebellum. Ma2 is a 40 kilodalton protein that is expressed in brain; the presence of antibodies to Ma2 (also referred to herein as "anti-Ta antibodies") is associated particularly with testicular cancer and the paraneoplastic syndromes paraneoplastic limbic encephalitis (PLE) and brainstem encephalitis (BE). Ma3 is a 21 kilodalton protein; Ma4 is a 36 kilodalton protein; and Ma5 is a 56 kilodalton protein.

POLYPEPTIDES OF THE INVENTION

Accordingly, the invention pertains to isolated Ma family polypeptides, as well as to polypeptide products encoded by nucleotide sequences described herein. The term "polypeptide" refers to a polymer of amino acids, and not to a specific length; thus, peptides, oligopeptides and proteins are included within the definition of a polypeptide. A "Ma family polypeptide," as used herein, refers to a polypeptide that is expressed by brain and/or testis, and that shares significant identity with Ma1, Ma2, Ma3, Ma4, and/or Ma5. A polypeptide that "shares significant identity" with is a polypeptide that has approximately 75% amino acid identity with Ma1, Ma2, Ma3, Ma4 and/or Ma5. Polypeptides exhibiting lower levels of identity are also useful and can be considered to be Ma family polypeptides, particular if they exhibit high, e.g., at least about 80%, more preferably at least about 90%, and even more preferably at least about 95%, amino acid identity with Ma1, Ma2, Ma3, Ma4 and/or Ma5 over one or more particular domains of the polypeptide. For example, polypeptides sharing high degrees of identity over domains necessary for particular activities, including antibody binding activity, are included herein.

In a preferred embodiment of the invention, the Ma family polypeptide is Ma1 (SEQ ID NO:4), Ma2 (SEQ ID NO:7), Ma3 (SEQ ID NO:9), Ma4 (SEQ ID NO:11), or Ma5 (SEQ ID NO:13). The term, "Ma family polypeptide," also includes a polypeptide that is expressed by brain and/or testis, and that is recognized by antibodies that specifically bind to Ma1, Ma2, Ma3, Ma4, and/or Ma5. The Ma family polypeptide of the invention can be partially or substantially purified (e.g., purified to homogeneity).

The Ma family polypeptides of the present invention can be isolated or purified (e.g., to homogeneity) from recombinant cell culture by a variety of processes. A polypeptide that is "isolated" is substantially free of naturally associated components, such as by separation from the components which accompany it in its natural state. Thus, a polypeptide which is chemically synthesized, or synthesized in a cellular system different from the cell in which it naturally originates, will be substantially free of naturally associated components, and thus, is considered to be "isolated". Methods of isolation include, but are not limited to, anion or cation exchange chromatography, ethanol precipitation, polyacrylamide gel electrophoresis, affinity chromatography and high performance liquid chromatography (HPLC). The particular method used will depend upon the properties of the polypeptide and the selection of the host cell; appropriate methods will be readily apparent to those skilled in the art.

According to the invention, the amino acid sequence of the Ma family polypeptide can be that of the naturally-occurring polypeptide (e.g., Ma1, SEQ ID NO:4, Ma2, SEQ ID NO:7, Ma3, SEQ ID NO:9, Ma4, SEQ ID NO:11, or Ma5, SEQ ID NO:13) or can comprise alterations therein.

Such alterations include conservative or non-conservative amino acid substitutions, additions and deletions of one or more amino acids; however, such alterations should preserve at least one activity of the Ma family polypeptide, i.e., the altered or mutant polypeptide should be an active or functional derivative of the naturally-occurring polypeptide. For example, the mutation(s) can preferably preserve the three dimensional configuration of an antibody binding site of the native polypeptide. Alternatively, the fragment retains other immunological activities, such as immunogenic function, as well as sharing of immunological epitopes for binding.

The presence or absence of Ma family polypeptide activity can be determined by various standard functional assays including, but not limited to, assays for binding of anti-Ma antibodies (i.e., antibodies to Ma1 or Ma2) or anti-Ta antibodies (i.e., antibodies to Ma2) to the polypeptide. Moreover, amino acids which are essential for the function of the Ma family polypeptide can be identified by methods known in the art. Particularly useful methods include identification of conserved amino acids in the superfamily of immunoglobulin genes, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

Other alterations of the Ma family polypeptides of the invention include, for example, glycosylations, acetylations, carboxylations, phosphorylations, ubiquitination, labelling (e.g., with radionuclides), enzymatic modifications, incorporation of analogs of an amino acid (including, e.g, natural amino acids), substituted linkages, and other modifications known in the art, both naturally and non-naturally occurring.

The invention described herein also relates to fragments of the isolated polypeptides described herein. The term "fragment" is intended to encompass a portion of a polypeptide described herein which retains one or more functions or biological activities of the isolated polypeptide, as described above (e.g., immunogenic or antigenic function). For example, the fragment can be from at least about 20 contiguous amino acids to at least about 200 contiguous amino acids, more preferably at least about 50 amino acids, even more preferably at least about 100 amino acids, even more preferably at least about 150 amino acids.

The Ma family polypeptide can also be a fusion protein comprising all or a portion of the Ma family polypeptide's amino acid sequence fused to one or more additional components. Representative fusion partners include immunoglobulins, bacterial β-galactosidase, trpE, protein A, β-lactamase, α-amylase, alcohol dehydrogenase, and yeast α mating factor. Additional components, such as radioisotopes and antigenic tags, can be selected to assist in the isolation or purification of the polypeptide or to extend the half life of the polypeptide; for example, a hexahistidine tag would permit ready purification by nickel chromatography. Furthermore, polypeptides of the present invention can be progenitors of the Ma family polypeptide; progenitors are molecules which are cleaved to form an active Ma family polypeptide.

Ma family polypeptides described herein can be isolated from naturally-occurring sources, chemically synthesized or recombinantly produced. For example, a nucleic acid molecule described herein can be used to produce a recombinant form of the encoded polypeptide via microbial or eukaryotic cellular processes. Ligating the polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant polypeptides according to the present invention by microbial means or tissue-culture technology.

NUCLEIC ACIDS OF THE INVENTION

The invention also pertains to isolated nucleic acid molecules encoding the Ma family polypeptides described above. Nucleic acid molecules of the present invention can be RNA (e.g., mRNA), or DNA, such as cDNA and genomic DNA. DNA molecules can be double-stranded or single-stranded; single stranded RNA or DNA can be either the coding (sense) strand or the non-coding (antisense) strand. Preferably, the nucleic acid molecule comprises at least about 15 nucleotides, more preferably at least about 30 nucleotides, even more preferably about 60 contiguous nucleotides, still more preferably at least about 100 contiguous nucleotides, even more preferably at least about 150 contiguous nucleotides, and even more preferably at least about contiguous 300 nucleotides. The nucleic acid molecule can be only that polynucleotide which encodes at least a fragment of the amino acid sequence of the Ma family polypeptide; alternatively, the nucleic acid molecule can include at least a fragment of the nucleic acid encoding the Ma family polypeptide along with additional non-coding sequences such as introns and non-coding 3' and 5' sequences (including regulatory sequences, for example). Additionally, the nucleic acid molecule can contain a marker sequence, for example, a nucleotide sequence which encodes a polypeptide, to assist in isolation or purification of the polypeptide. Such sequences include, but are not limited to, those which encode a glutathione-S-transferase (GST) fusion protein and those which encode a hemagglutinin A (HA) peptide marker from influenza. In a preferred embodiment, the nucleic acid molecule has the sequence encoding Ma1 (SEQ ID NO:3); the sequence encoding Ma2 (SEQ ID NO:6); the sequence encoding Ma3 (SEQ ID NO:8); the sequence encoding Ma4 (SEQ ID NO:10); or the sequence encoding Ma5 (SEQ ID NO:12).

As used herein, an "isolated" or "substantially pure" nucleic acid molecule is intended to mean a nucleotide sequence which is not flanked by nucleotide sequences which normally (in nature) flank the gene or nucleotide sequence (as in genomic sequences) and/or has been completely or partially purified from other transcribed sequences (as in a cDNA or RNA library). Thus, an isolated nucleotide sequence can include a nucleotide sequence which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the Ma family polypeptide in tissue (e.g., human tissue), such as by Northern blot analysis.

The present invention also pertains to nucleic acid molecules which are not necessarily found in nature but which encode the Ma family polypeptide. Thus, DNA molecules which comprise a sequence that is different from the naturally-occurring nucleotide sequence but which, due to the degeneracy of the genetic code, encode the Ma family polypeptide of the present invention are the subject of this invention (e.g., a nucleic acid molecule that encodes SEQ ID NO:4, SEQ ID NO:7, SEQ ID NO:9, SEQ ID NO:11, or SEQ ID NO:13). The invention also encompasses variations of the nucleotide sequences of the invention, such as those encoding portions, analogues or derivatives of the Ma family polypeptide. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the Ma family polypeptide.

Other alterations of the nucleic acid molecules of the invention can include, for example, labelling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequences via hydrogen bonding and other chemical interactions. Such molecules include, for example, those in which peptide linkages substitute for phosphate linkages in the backbone of the molecule.

The invention also relates to fragments of the isolated nucleic acid molecules described herein. The term "fragment" is intended to encompass a portion of a nucleic acid sequence described herein, such as a portion which encodes a fragment of a Ma family polypeptide as described above. For example, a fragment can be a portion of a nucleic acid which is from at least about 15 contiguous nucleotides to at least about 300 contiguous nucleotides or longer in length. One or more introns can also be present. Such fragments are useful as probes, e.g., for diagnostic methods and also as primers or probes. Particularly preferred primers and probes selectively hybridize to the nucleic acid molecule encoding the Ma family polypeptides described herein. For example, fragments which encode antigenic regions of the Ma family polypeptides described herein are useful.

The invention also pertains to nucleic acid molecules which hybridize under medium, and, more preferably, high, stringency hybridization conditions (e.g., for selective hybridization) to a portion of a nucleic acid molecule described herein. Appropriate stringency conditions are known to those skilled in the art or can be found in standard texts such as *Current Protocols in Molecular Biology*, John Wiley & Sons, New York (1998), 6.3.1–6.3.6. Such hybridizable nucleic acid molecules are useful as probes and primers for diagnostic applications. For example, high stringency hybridization conditions for Southern blotting include conditions with a temperature that is from about 12–20° C. below the calculated Tm (Tm is based upon the nucleotide sequence of the probe and can be calculated for each probe); alternatively, high stringency conditions include low salt conditions.

Accordingly, the invention pertains to nucleic acid molecules that have a substantial identity with the nucleotide sequences described herein. Particularly preferred are nucleic acid molecules which have at least about 60%, more preferably at least about 85%, even more preferably at least about 95%, and still more preferably at least about 99% identity with nucleotide sequences described herein. Also particularly preferred in this instance are nucleic acid molecules encoding polypeptides having at least one activity of the Ma family polypeptides described herein. For example, preferred nucleic acid molecules encoding a polypeptide having the same or similar immunogenic or antigenic properties as the Ma family polypeptide are within the scope of the invention. Nucleic acid molecules which have lower overall homologies are also included herein, provided that they have substantial identity over fragments of the polypeptide. For example, the Ma family polypeptides each contain segments (ranging from approximately 15 nucleotides to approximately 100 nucleotides, with segments up to 120 and to 360 nucleotides) having substantial homology (ranging from at least 60% to at least 95%) with one another. Ma1 and Ma2 share substantial identity, ranging from 60% to 76.5%, over five separate segments: nucleotides 11–38 of Ma2 and 678–705 of Ma1 (71.4% homology); nucleotides 78–109 of Ma2 and 745–776 of Ma1 (68.8% homology); nucleotides 150–165 of Ma2 and 814–829 of Ma1 (60% homology); nucleotides 184–200 of Ma2 and 846–864 of Ma1 (76.5% homology); and nucleotides 246–341 of Ma2 and 910–1005 of Ma1 (74% homology). The substantial homology over several segments indicates that the encoded polypeptides are closely related. Thus, nucleic acid molecules which similarly have lower overall homology to a Ma family polypeptide, but which have substantial homology to one or more regions of the Ma family polypeptide, are encompassed by the invention.

The invention also provides expression vectors containing a nucleotide sequence encoding a Ma family polypeptide or active derivative or fragment thereof, operably linked to at least one regulatory sequence. Many such vectors are commercially available, and other suitable vectors can be readily prepared by the skilled artisan. "Operably linked" is intended to meant that the nucleotide sequence is linked to a regulatory sequence in a manner which allows expression of the nucleotide sequence. Regulatory sequences are art-recognized and are selected to produce a Ma family polypeptide or active derivative thereof. Accordingly, the term "regulatory sequence" includes promoters, enhancers, and other expression control elements which are described in Goeddel, *Gene Expression Technology: Methods in Enzymology* 185, Academic Press, San Diego, California (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides encoded by the nucleic acid molecules of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Vectors can also include, for example, an autonomously replicating sequence (ARS), expression control sequences, ribosome-binding sites, RNA splice sites, polyadenylation sites, transcriptional terminator sequences, secretion signals and mRNA stabilizing sequences.

Prokaryotic and eukaryotic host cells transformed by the described vectors are also provided by this invention. For instance, cells which can be transformed with the vectors of the present invention include, but are not limited to, bacterial cells such as *E. coli* (e.g., *E. coli* K12 strains), Streptomyces, Pseudomonas, *Serratia marcescens and Salmonella typhimurium*, insect cells (baculovirus), including Drosophila, fungal cells, such as yeast cells, plant cells and mammalian cells, such as thymocytes, Chinese hamster ovary cells (CHO), and COS cells. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host.

The nucleic acid molecules of the present invention can be produced, for example, by replication in a suitable host cell, as described above. Alternatively, the nucleic acid molecules can also be produced by chemical synthesis.

ANTIBODIES OF THE INVENTION

The present invention also relates to isolated antibodies, or antigen-binding fragments, which bind to a Ma family polypeptide (or polypeptides). For instance, polyclonal and monoclonal antibodies, including non-human and human antibodies, humanized antibodies, chimeric antibodies and antigen-binding fragments thereof (*Current Protocols in Immunology*, John Wiley & Sons, New York (1994); EP Application 173,494 (Morrison); International Patent Application WO86/01533 (Neuberger); and U.S. Pat. No. 5,225,539 (Winters)) which bind to the described Ma family polypeptides are within the scope of the invention. A mammal, such as a mouse, rat, hamster or rabbit, can be immunized with an immunogenic form of the Ma family polypeptide (e.g., the protein or a peptide comprising an antigenic fragment of the protein which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and F(ab)$_2$'. Such antibodies, in conjunction with a label, such as a radioactive label, can be used to assay for the presence of the expressed protein in a cell from, e.g., a tissue sample. Such antibodies can also be used in an immunoabsorption process, such as an ELISA, to isolate the Ma family polypeptide. Tissue samples which can be assayed include primate, particularly human, tissues, e.g., differentiated and non-differentiated cells. Examples include brain and testis.

METHODS OF DIAGNOSIS OF THE INVENTION

Because of the relationship between the Ma family polypeptides Ma1 and Ma2 with paraneoplastic syndromes, methods are now available for diagnosing the presence or absence of a paraneoplastic syndrome in an individual, by assessing a test sample from an individual for the presence or absence of antibodies to Ma family polypeptide(s). The presence of antibodies to a Ma family polypeptide is indicative of the presence of a paraneoplastic syndrome; the absence of antibodies to a Ma family polypeptide is indicative of the absence of the paraneoplastic syndrome. The term, "paraneoplastic syndrome," as used herein, refers to a neurologic disorder that is associated with the presence of a neoplasm (cancer), but is not due to direct invasion of the nervous system by the neoplasm or due to other complications such as side effects of treatment, infections, metabolic and nutritional deficits and cerebrovascular disorders. In a preferred embodiment, the presence of antibodies that bind to the Ma family polypeptide, Ma1, is indicative of a paraneoplastic syndrome. In another preferred embodiment, the presence of antibodies that bind to the Ma family polypeptide, Ma2, is indicative of a paraneoplastic syndrome. In a particularly preferred embodiment, the presence of antibodies that bind to Ma2 is indicative of the paraneoplastic syndrome(s), paraneoplastic limbic encephalitis and/ or brainstem encephalitis. The presence of antibodies that bind to more than one Ma family polypeptide (e.g., to both Ma1 and Ma2) is also indicative of the presence of a paraneoplastic syndrome.

In addition, methods are now available for diagnosing the presence or absence of a neoplasm in an individual, by assessing a test sample from an individual for the presence or absence of antibodies to Ma family polypeptide(s). Because paraneoplastic syndromes often occur prior to discovery of the underlying neoplasm, these methods facilitate identification of the presence of a neoplasm by identifying a neurologic disorder as a paraneoplastic syndrome. In addition, antibodies to a Ma family polypeptide(s) may be present in an individual (e.g., at low levels) in the absence of paraneoplastic pathology (i.e., in the absence of a paraneoplastic syndrome); the methods of the invention facilitate identification of the presence of a neoplasm in these individuals as well. The presence of antibodies to a Ma family polypeptide is indicative of the presence of a paraneoplastic syndrome, and therefore is indicative of the presence of a neoplasm. In a preferred embodiment, the presence of antibodies that bind to the Ma family polypeptide Ma1 (e.g., anti-Ma antibodies), is indicative of the presence of a neoplasm. In a particularly preferred embodiment, the neoplasm is breast cancer, colon cancer, lung cancer, testicular cancer, a germ cell tumor or parotid gland cancer. In another preferred embodiment, the presence of antibodies that bind to the Ma family polypeptide Ma2 (e.g., anti-Ta antibodies) is indicative of the presence of a testicular neoplasm and/or a germ cell tumor. The absence of antibodies to a Ma family polypeptide is indicative of the absence of a paraneoplastic syndrome, and therefore is indicative of the absence of a neoplasm.

In the methods of the invention, a test sample from an individual, such as an individual who is suspected of having a paraneoplastic syndrome, is used. The test sample can also be from an individual who is suspected of having a cancer, but who does not demonstrate a paraneoplastic syndrome. The test sample can comprise blood, serum, cerebrospinal fluid, urine, nasal secretion, saliva, or any other bodily fluid or tissue. Alternatively, the test sample can comprise antibodies isolated from a sample of bodily fluid or tissue from the individual. If the sample is isolated antibodies, the isolated antibodies can include a single type of antibody (e.g., IgA, IgD, IgE, IgG or IgM antibodies), or can include all types of antibodies; alternatively, one or more types of antibodies (e.g., IgM antibodies, IgG antibodies, or IgM and IgG antibodies) can be isolated. In a preferred embodiment, the test sample is a serum sample or a cerebrospinal fluid sample from the individual.

The test sample is assessed for the presence or absence of antibodies that bind to a Ma family polypeptide (or to more than one Ma family polypeptide). In one embodiment of the invention, one or more of the Ma family polypeptides described above can be used to detect the presence of antibodies to the Ma family polypeptide. In these methods, a Ma family polypeptide sample is used. The term, "Ma family polypeptide sample," as used herein, can be a sample containing a Ma family polypeptide, or active derivative or fragment thereof, as described above. The Ma family polypeptide sample can also contain more than one Ma family polypeptide or active derivative or fragment (e.g., a Ma family polypeptide sample containing Ma1 and Ma2). In a preferred embodiment, the Ma family polypeptide sample comprises Ma1 and/or Ma2. The Ma family polypeptide sample can be a sample of isolated Ma family polypeptide(s); alternatively, the Ma family polypeptide sample can be a sample that comprises Ma family polypeptide(s) (e.g., slice(s) of tissue, such as neuronal tissue from human brain or rat brain, or another tissue known to contain the Ma family polypeptide(s), or a homogenate of tissue(s) known to contain the Ma family polypeptide(s)).

The Ma family polypeptide sample is contacted with the test sample from an individual. Contact of the Ma family polypeptide sample with the test sample from the individual results in a "contacted sample," which is a mixture of the Ma family polypeptide sample and the test sample. The contacted sample is maintained under appropriate conditions to allow binding of antibody to Ma family polypeptide, if such antibody is present in the sample, to the Ma family polypeptide. The terms, "anti-Ma family polypeptide antibody" or "anti-Ma family polypeptide autoantibody", as used herein, refer to antibody that specifically binds to a Ma family polypeptide as described above. The presence or absence of anti-Ma family polypeptide antibody is then assessed.

In one embodiment of the invention, the amount of anti-Ma family polypeptide antibodies, if any, that have bound to the Ma family polypeptide in the contacted sample, is compared to a reference amount. The term, "reference amount," as used herein, refers to an amount of anti-Ma family polypeptide antibodies that correlates with a diagnosis of an paraneoplastic syndrome or of a neoplasm. A reference amount can be determined, for example, by comparing amounts of anti-Ma family polypeptide antibodies in contacted samples from individuals known to have a paraneoplastic syndrome (e.g., a "positive control sample"), with amounts of anti-Ma family polypeptide antibodies in contacted samples from individuals known not to have a paraneoplastic syndrome (e.g., a "negative control sample" as described below), and determining what amount of antibody correlates with disease. The reference amount can be determined by determining the amounts of anti-Ma family polypeptide antibodies in positive and/or negative control samples concurrently with determining the amount of anti-Ma family polypeptide antibodies in the contacted sample; alternatively, the reference amount can be a historically determined amount (i.e., an amount determined prior to determining the amount of anti-Ma family polypeptide antibodies in the contacted sample). For example, in one embodiment, a "reference amount" can be an amount of anti-Ma family polypeptide antibody in the test sample that statistically is significantly greater than the amount of anti-Ma family polypeptide antibody in comparable control sample(s). In one embodiment, an amount of anti-Ma family polypeptide in the test sample is statistically significant when it is two standard deviations greater than the amount of anti-Ma family polypeptide antibody in comparable control samples.

The amount of different types of antibodies (i.e., a sum including the amount of more than one type of antibody) can be compared to the reference amount; alternatively, the amount of one particular type of antibody (e.g., the amount of IgA, IgD, IgE, IgM or IgG antibody) can be compared to the reference amount. In a preferred embodiment, the antibody is IgG antibody. The reference amount is an amount of the same type of antibody as the antibody assessed in the contacted sample: for example, if the sum of the amount of different types of antibodies (i.e., including more than one type of antibody) for the contacted sample is compared to the reference amount, the sum of the amount of those types of antibodies is also used for the reference amount. If the amount of one particular type of antibody (e.g., the amount of IgM or IgG antibodies) in the contacted sample is compared with the reference amount, the amount of that type of antibodies is also used for the reference amount.

In one embodiment, the presence of an amount that is equal to, or greater than, the reference amount correlates with a diagnosis of (is indicative of the presence of) paraneoplastic syndrome. Similarly, the presence of an amount that is equal to, or greater than, the reference amount correlates with the presence of a neoplasm. An amount that is less than the reference amount correlates with (is indicative of) an absence of paraneoplastic syndrome. Similarly, the presence of an amount that is less than the reference amount correlates with the absence of a neoplasm.

In another embodiment of the invention, the contacted sample is assayed to determine the amount of anti-Ma family polypeptide antibodies, if any, that have bound to the Ma family polypeptide. The assay can determine an amount that is the sum of the amount of different types of antibodies (i.e.,including more than one type of antibody); alternatively, the assay can determine the amount of one particular type of antibody (e.g., the amount of IgA, IgD, IgE, IgM or IgG antibody). In a preferred embodiment, the contacted sample is assayed to determine the amount of IgM or IgG antibody.

The amount of anti-Ma family polypeptide antibody in the contacted sample is compared with the amount of anti-Ma family polypeptide antibody in at least one comparable negative control sample (i.e., a sample from an individual who is not afflicted by a paraneoplastic syndrome). The negative control sample can be a sample from any individual who is not afflicted with a paraneoplastic syndrome. It is not necessary that the negative control sample be from an individual who is free of disease: for example, the negative control sample can be a sample from an individual who has cancer but no paraneoplastic syndrome. A "comparable" negative control sample is a sample of the same type of body fluid or tissue as the test sample; alternatively, if the test sample is antibodies isolated from a sample of fluid or tissue, the comparable negative control sample is a sample of antibodies isolated from the same type of bodily fluid or tissue. More than one control sample can be used. The assay of the negative control sample determines the same type of antibody as the assay of the contacted sample: for example, if the sum of the amount of different types of antibodies (i.e., including more than one type of antibody) is detected for the contacted sample, the sum of the amount of those types of antibodies is also determined for the negative control sample. If the assay determines the amount of one particular type of antibody (e.g., the amount of IgM or IgG antibodies) in the contacted sample, the amount of that type of antibodies is also determined for the negative control sample. In a preferred embodiment, more than one control sample can be used.

The amount of antibody, or the presence or absence of antibody, can be determined by a variety of methods using standard techniques, including enzyme-linked immunosorbent assay (ELISA) or other solid phase immunoassays, radioimmunoassay, nephelometry, electrophoresis, inununofluorescence, Western blot (immunoblot), or other methods (see Ausubel, F. M. et al., eds., Current Protocols in Molecular Biology, John Wiley & Sons, including supplements through 1997, especially units 11.2 (ELISA) and 11.16 (Determination of Specific Antibody Titer)). In a preferred embodiment, the titer is determined by ELISA; in another preferred embodiment, the amount (or presence or absence) of antibody is determined by Western blot. For example, the amount (or presence or absence of antibody) can be determined by using section(s) of neuronal tissue, such as human and/or rat brain, as the Ma family polypeptide sample; the sections are incubated with the test samples, and then presence or absence, or amount, of anti-Ma family polypeptide antibodies, can be assessed by an appropriate method, such as by a detector antibody or indirect immunofluorescence. In another example, the amount (or presence or absence of antibody) can be determined by using homogenized neuronal tissue, and separating the proteins on a Western blot; the blot is then incubated with the test samples, and then presence or absence, or amount, of anti-Ma family polypeptide antibodies, can be assessed by an appropriate method, such as by a detector antibody or indirect immunofluorescence. The presence of a protein band at an appropriate weight (e.g., at the molecular weight of the Ma family polypeptide) is indicative of the presence of anti-Ma family polypeptide antibodies. In a particularly preferred embodiment, the Ma family polypeptide is attached to a solid support. Typically, the amount of antibody that binds to the Ma family polypeptide sample can be determined using a detector antibody that binds to the anti-Ma family polypeptide antibody.

The presence of an amount of anti-Ma family polypeptide antibody in the test sample that is significantly greater than the amount of anti-Ma family polypeptide antibody in a comparable control sample(s), correlates with the presence of a paraneoplastic syndrome. The presence of an amount of anti-Ma family polypeptide antibody in the test sample that is not significantly greater than the amount of anti-Ma family polypeptide antibody in a comparable control sample(s), correlates with an absence of a paraneoplastic syndrome. For example, if immunohistochemistry is used, the presence of greater reactivity in serum of a patient diluted 1:500, than in a control sample(s), correlates with a diagnosis of paraneoplastic syndrome; the absence of visible reactivity in serum of a patient diluted 1:500, is indicative of the absence of paraneoplastic syndrome. In another embodiment, if Western blotting is used, the presence of greater reactivity in serum of a patient diluted 1:1,000, than in a control sample(s), correlates with a diagnosis of paraneoplastic syndrome; the absence of visible reactivity in serum of a patient diluted 1:1,000, correlates with the absence of paraneoplastic syndrome. Similarly, the presence of an amount of anti-Ma family polypeptide antibody in the test sample that is significantly greater than the amount of anti-Ma family polypeptide antibody in a comparable control sample(s), correlates with the presence of a neoplasm. The presence of an amount of anti-Ma family polypeptide antibody in the test sample that is not significantly greater than the amount of anti-Ma family polypeptide antibody in a comparable control sample(s), correlates with the absence of a neoplasm.

The present invention also includes kits to be used in methods of the invention. Kits can include the following components: (1) a Ma family polypeptide sample; and, optionally, (2) labeled detector antibody that binds to antibody, preferably to the anti-Ma family polypeptide antibody. Detector antibody can comprise an antibody bound to a detectable agent, such as an enzyme, radioactive molecule, or fluorescent agent. If the detector antibody is bound to an enzyme that reacts with an added substrate to yield a colored product, such as horseradish peroxidase, the kit can also include the substrate. The Ma family polypeptide sample in the kit can be adhered to a solid support.

The following Examples are offered for the purpose of illustrating the present invention and are not to be construed to limit the scope of this invention. The teachings of all references cited herein are hereby incorporated herein by reference.

EXAMPLES

Example 1

Identification of Ma1, A Neuronal and Testis Specific Protein that is Recognized By the Serum of Patients With Paraneoplastic Neurologic Disorders The serum of patients with suspected paraneoplastic syndromes was examined for antineuronal antibodies. A novel antineuronal antibody (called anti-Ma) was identified in the serum of four patients with paraneoplastic neurologic syndromes. Identification of the expression of the target antigens in rat and normal human tissues and tumors, and cloning of Ma1, a novel neuronal and testis specific protein recognized by anti-Ma sera, were performed as described below.

A. Material and Methods

Patients, Sera and Tissues

The sera (or cerebrospinal fluid when available) from 1,705 patients that were sent to be screened for paraneoplastic antineuronal antibodies were used in a study. At the time that these sera were collected, 984 of the patients had a cancer diagnosis. Sera used as controls included sera from 52 normal individuals; sera from 96 patients with well characterized paraneoplastic syndromes (44 anti-Hu related encephalomyelitis and sensory neuronopathy; 17 anti-Yo related cerebellar degeneration; 11 Lambert-Eaton myasthenic syndrome with P/Q-type voltage gated calcium-channel antibodies [VGCC]; 2 anti-Ri related cerebellar ataxia and opsoclonus; 6 anti-Tr related cerebellar dysfunction; 5 myasthenia gravis associated with thymoma; and 11 opsoclonus associated with neuroblastoma); sera from 179 patients with cancer (44 testicular, 10 colon, 10 ovarian, 40 lung, 22 breast, 20 brain tumors, and 33 neuroblastomas) but without paraneoplastic neurologic syndromes; sera from 6 patients with amyotrophic lateral sclerosis without cancer; and sera from 4 patients with myasthenia gravis without thymoma.

Sera were kept frozen at −70° C. Human nervous system and systemic tissues were obtained from autopsy or biopsy studies of neurologically normal individuals. Fifty three cancer tissues (15 colon, 5 breast, 5 bladder, 3 parotid, 5 neuroblastomas, 5 non-small cell lung cancer, and 15 testicular germ cell tumors) from patients without paraneoplastic symptoms and 13 from patients with antibody associated paraneoplastic disorders (4 ovary, 4 lung, 2 uterus, 1 bladder, 1 larynx and 1 chondrosarcoma) were provided by the Tumor Procurement Service at Memorial Sloan-Kettering Cancer Center.

Wistar rats were anesthetized and perfused with saline, followed by removal of brain and other tissues. Samples of human and rat tissues were kept at −70° C.; other samples from the same tissues were embedded in Optimal Cutting Temperature medium (OCT, Miles Inc, USA) and frozen in isopentane chilled by liquid nitrogen.

For studies of human tumors and immunohistochemical competition assays, the IgG from patients' sera was isolated using a protein-G sepharose column (Sigma, St Louis, Missouri) followed by labeling with biotin (Furneaux, H. M. et al., *New Engl. J Med.* 322:1844–1851 (1990)).

For Western blot analysis, human tissues were homogenized in 0. 1% Nonidet P-40 and protease inhibitors: PMSF (50 $\mu$g/ml), aprotinin (1 $\mu$g/ml), pepstatin (1 $\mu$g/ml), and leupeptine (1 $\mu$g/ml) (all from Sigma).

Immunohistochemistry

Seven micron-thick frozen sections of rat and human brain and cerebellum were fixed in formalin, 100% methanol, or cold acetone (4° C.) and sequentially incubated with 0.3% hydrogen peroxide in phosphate buffered saline (PBS) for 10 minutes, 10% normal goat serum for 20 minutes, the patient's serum diluted at 1:500 for 2 hours, biotinylated goat anti-human IgG (Vector, Burlingame, Calif.) diluted 1:2,000, for 30 minutes, and the avidin biotin peroxidase complex (Vector) for 30 minutes. The reaction was developed with 0.05% diaminobenzidine tetrahydrochloride (Sigma) with 0.01% hydrogen peroxide and 0.5% Triton X-100 in PBS. Patient's serum and secondary antibody were diluted in 10% normal goat serum in PBS. Between steps, slides were washed with PBS.

To avoid reactivity with endogenous IgG, all immunohistochemical studies on systemic human tissues and tumors utilized biotinylated IgG isolated from the patients' sera. All steps were done as above except that preincubation of the sections with 10% normal human serum was used to block nonspecific IgG binding, and no secondary antibody was used.

For competition assays, tissue sections were preincubated with the serum of one of the patients (diluted 1:5) for one hour, followed by incubation with biotinylated IgG isolated from the serum of another patient (diluted 1:25). Tissues preincubated with normal human serum or serum from patients with other antineuronal antibodies (diluted 1:5) served as controls. Sera were considered to compete for the same epitopes, when the reactivity of the biotinylated IgG of one patient was abrogated by preincubation of the tissue with serum from another patient.

Screening of a Cerebellar cDNA Expression Library

A λZAP human cerebellar library (Stratagene, La Jolla, Calif.) was screened at a density of 5×10⁴ pfu/150 mm plate. After a 3 hour incubation at 42° C., plates were overlaid with filters soaked in 10 mmol/L isopropyl β-D-thiogalactopyranoside (IPTG) and incubated for 4 hours at 37° C. Plates were then cooled for 20 minutes at 4° C., and filters were removed, blocked with 1% bovine serum albumin (BSA) for 12 hours at 4° C., and incubated for 3 hours with serum (diluted 1:1,000) from a patient with paraneoplastic brainstem and cerebellar dysfunction. After washing with Tween-20, filters were incubated with $I^{125}$ protein A (0.1 μCi/mL) for 1 hour, washed, dried and exposed to XAR5 film for 24 hours at −70° C. Clones giving positive results were purified by several rounds of antibody screening until a yield of 100% positive plaques was obtained. Phage clones were subcloned in pBluescript using the in vivo excision phage rescue protocol (Stratagene).

DNA Sequencing

Sequence analysis was performed with an automated DNA sequencer (ABI 377) using the dye terminator fluorescence method (Lee, L. G. et al., *Nucl. Acids Res.* 20:2471–2483 (1992)). Double-stranded DNA was purified using the Qiagen plasmid midi-prep system (Qiagen, Santa Clarita, Calif.) and sequenced on both strands. Internal oligonucleotide primers, as well as SK and KS primers, were used.

Western Blot Analysis

Fusion protein and *E. coli* protein extracts were obtained by growing an individual colony to an optical density of 0.6 and inducing with 10 mmol/L IPTG for 3 hours at 37° C. Cells were isolated by centrifugation and lysed by resuspension in 0.1% NP-40 and 2% sodium dodecyl sulfate (SDS) in PBS.

Lysates of fusion proteins, or proteins extracted from human and rat tissues, were resolved by 10% SDS-polyacrylamide gel electrophoresis and transferred to nitrocellulose (Towbin, H. et al., *Proc. Natl. Acad. Sci. USA* 76:4350–4 (1979)). After blocking with 5% dry Carnation™ milk, nitrocellulose strips were sequentially incubated with the patient's serum (1:1,000 dilution) for 2 hours, and sheep anti-human horseradish peroxidase-labeled IgG (Amersham, Arlington Heights, Ill. diluted 1:20,000, for one hour. Strips were then immersed in an enhanced chemiluminescence solution (Amersham, Arlington, Ill.) for 1 minute, and exposed to Kodak XAR5 film (Sigma). Between steps, strips were washed with 0.05% Tween-20 in PBS. All incubations were done at room temperature (RT).

Northern Blot Analysis

Sequence specific oligonucleotide probes were end-labeled with $[\gamma-^{32}P]$ ATP using T4 polynucleotide kinase. As probe for Ma1, the following oligonucleotide was used: 5'-GAAACCCAAGGACACGGG-3' (SEQ ID NO:1; cDNA base pairs 647–630), and as probe for β-actin, the following oligonucleotide was used: 5'-GTCTTTGCGGATGTCCACG-3' (SEQ ID NO:2). Labeled probes were extracted with phenol chloroform and purified over a G-25 sephadex column. Probes (1×10⁷ cpm/mL) were hybridized to "Human Multiple Tissue Northern Blots I and II" (Clontech, Palo Alto, Calif.) overnight at 42° C. in Rapid Hyb buffer (Amersham). Blots were washed for 15 minutes at RT in 5×SSC (20X=NaCl 3M and Na₃Citrate 0.3M, pH 7.0), 0.1% SDS; at 42° C. in 1×SSC, 0.1% SDS; and at 42° C. in 0.1×SSC, 0.1% SDS. After hybridization with the Ma1 probe, blots were stripped by boiling in 0.5% SDS for 10 minutes and hybridized with β-actin probe. For visualization, blots were exposed to XAR film for 72 hours at −80° C.

B. Results

Clinical and Pathological Findings

The study of 1,705 sera resulted in the identification of 4 patients who harbored a novel antineuronal antibody, that is called anti-Ma. The clinical information of these patients is summarized in Table 1.

TABLE 1

Clinical Features of 4 Patients with Paraneoplastic Syndromes

| Patient, Sex, age | Time from PNS to tumor diagnosis | First neurological symptom(s) | Paraneoplastic syndrome | Tumor, Stage (Expression of Ma Ags) | Neurological treatment | Outcome | Autopsy |
|---|---|---|---|---|---|---|---|
| Patient 1 F, 63 | 6 months | Gait difficulty, poor arm coordination, slurred speech, head tremor | Pancerebellar syndrome (unable to walk), dysphagia, oscillopsia, absent reflexes (both knees and right ankle). Vibratory loss in toes. | Parotid, limited. (Ma Ag+) | IVIg, Protein A column | Stable, 2 years after first symptom | — |
| Patient 2 F, 63 | Preceded (? Months) cancer reoccurence | Ataxia of extremities | Cerebellar dysfunction | Breast, extensive. (Ma Ag+) | None | Dead, from systemic complications | Severe loss of Purkinje cells & Bergmann gliosis. Inflammatory infiltrates of T cells in the cerebellar white matter. |
| Patient 3 M, 58 | 1 year | Dysphagia | Dysphagia, mild proximal weakness, absent ankle reflexes, decreased vibratory and temperature sensation in feet, impotence. | Large-cell cancer of the lung, limited. (Ma Ag, not studied) | Tumor resection | Lost to follow-up | — |

TABLE 1-continued

Clinical Features of 4 Patients with Paraneoplastic Syndromes

| Patient, Sex, age | Time from PNS to tumor diagnosis | First neurological symptom(s) | Paraneoplastic syndrome | Tumor, Stage (Expression of Ma Ags) | Neurological treatment | Outcome | Autopsy |
|---|---|---|---|---|---|---|---|
| Patient 4 F, 58 | 11 months | Diplopia, unsteadiness, pseudobulbar affect | Abolished vertical eye movements; limited adduction of left eye, dysarthria, myokymia and decreased sensation on left side of the face, wide-base gait. Mild cognitive deficit. | Colon, limited. (Ma Ag+) | IVIg, Plasma exchange, Prednisone | Dead, from neurologic disease | Neuronal loss & gliosis involving: brainstem, Purkinje cells, the dentate nucleus of the cerebellum. T-cell infiltrates & microglial nodules: brainstem (mainly medulla), cerebellar white matter, hypothalamus, substantia innominata. |

PNS: Paraneoplastic symptoms;
Ma Ags: Ma antigens;
IVIg: Intravenous immunoglobulin Neurologic symptoms preceded the diagnosis of the tumor in 3 patients, and preceded recurrence of a breast cancer diagnosed 6 years earlier in 1 patient. Three patients had symptoms of cerebellar and/or brainstem involvement; the associated cancers were breast, parotid, and colon. Another patient with a history of mild dysphagia, proximal weakness and sexual impotence for one year, underwent mediastinoscopy and biopsy of a large cell carcinoma of the right bronchus; after anesthesia he developed respiratory muscle weakness. Neurophysiological studies and serological test (P/Q-type voltage gated calcium channel antibodies) for the Lambert-Eaton myasthenic syndrome, were negative. This patient was lost to follow-up and it is not known if he developed other neurological symptoms.

Among the three patients with available clinical information, two received immunomodulatory treatments (intravenous immunoglobulin, protein A column immunoabsorption, plasma exchange), but none improved the neurologic deficits. One patient is alive and two are dead, one from multiple systemic problems (peritoneal carcinomatosis, sepsis, coagulopathy), the other from progressive brainstem dysfunction.

At autopsy, one patient had extensive systemic metastases of breast cancer, and micronodular cirrhosis. No metastases were identified in the nervous system (spinal cord not examined). There was almost complete absence of Purkinje cells in the cerebellum, associated with Bergmann gliosis, and mild inflammatory infiltrates in the deep cerebellar white matter. Neuritic plaques were identified in cortex (mainly in the occipital lobe), but no other abnormalities were found in cerebral cortex, amygdala and brainstem. This patient had no history suggesting Alzheimer's disease.

The autopsy of the other patient was restricted to brain, and the possibility of clinically undetected systemic metastases could not be ruled out. The tectal and tegmental regions of the midbrain, pontine tegmentum, and medulla showed extensive perivascular and interstitial inflammatory infiltrates with microglial nodules. Severe neuronal loss and gliosis were found in the inferior olivary nucleus and surrounding tissue. There was also focal loss of Purkinje cells and of neurons of the dentate nucleus, with Bergmann gliosis. Inflammatory infiltrates were found in the deep cerebellar white matter. Milder perivascular and interstitial lymphocytic infiltrates were observed in the hypothalamus and substantia innominata.

In both patients, immunohistochemical analysis of the inflammatory infiltrates with markers for B (CD20) cells, T (CD3) cells, and subtypes of T cells (CD4 and CD8), demonstrated that most (>90%) of the cells were T-lymphocytes, mainly CD8+(>75% of T-cells).

Laboratory Findings

Anti-Ma Antibodies Specifically React With Normal Brain and Testis

The sera of the above 4 patients reacted with all neurons of the central and peripheral nervous system, including sympathetic and dorsal root ganglia, and myenteric plexus, in a characteristic pattern. Anti-Ma antibodies reacted mainly within subnuclear elements (nuclei and nucleoli) of neurons, and to a lesser degree with the cytoplasm. Non-neuronal cells did not react. Reactivity was not affected by formalin, methanol, or acetone fixation, but it was better preserved in frozen tissues than in paraffin embedded tissues. In frozen rat tissue, the neuronal nuclei showed a speckled pattern of reactivity, and in many neurons it appeared confined to the nucleoli; in contrast, the cytoplasm reacted in a mild and diffuse, but not granular, pattern. In frozen and paraffin embedded human tissues, the reactivity appeared more concentrated to the nucleoli of neurons, and there was also mild labeling of the cytoplasm. Human and rat systemic tissues, including lung, liver, kidney, spleen, thyroid gland, pancreas, small intestine, colon, heart, skeletal muscle and ovary did not react with anti-Ma IgG, but testicular germ cells, especially spermatocytes and early spermatids, did react. In rat testis, there was speckled staining selectively involving the germ cells of the seminiferous tubule, but no labeling of the Leydig cells in the interstitium was observed. Anti-Ma labeling in human testicular germ cells was restricted to a few dots of nuclear reactivity, with milder, diffuse staining of the nucleus and cytoplasm.

In immunoblots of protein extracts from the same systemic tissues, brain homogenates, and purified neurons (cortical neurons and Purkinje cells), the 4 anti-Ma sera reacted with proteins expressed only in purified neurons and homogenates of brain and testis. In brain, two distinct bands of reactivity were identified at 37 and 40 kDa. In testis, only the 37 kDa protein was found. None of the 337 control sera showed the above immunohistochemical and Western blot reactivities.

Anti-Ma Antibodies Specifically Recognize Paraneoplastic Tumors

Paraffin-embedded tumor tissue was obtained from 3 of the 4 patients with anti-Ma antibodies. After tissue deparaffination and antigen retrieval (Cattoretti, G. et al., *J. Pathol.* 171:83–98 (1993)), all 3 tumors (adenocarcinoma of the breast, adenocarcinoma of the colon and parotid cancer)

were found to express antigens identified by anti-Ma IgG antibodies, but in contrast to neurons the reactivity was concentrated in the cytoplasm. Anti-Ma antibodies reacted with the cytoplasm of the tumor cells; no reactivity was identified with normal human IgG antibodies.

The expression of Ma antigens was also examined in frozen or paraffin embedded tumors, including 53 tumors from patients without paraneoplastic syndromes and 13 tumors from patients with other antibody associated paraneoplastic symptoms: none reacted with anti-Ma antibodies.

Initial immunohistochemical findings were reproduced using biotinylated anti-Ma IgG from two different patients, and further confirmed by a competition assay in which preincubation of tissues with any of the anti-Ma sera abrogated the reactivity of the biotinylated IgG from another anti-Ma patient.

C. Cloning and Characterization of the Ma1 Antigen

Cloning of the Ma1 Antigen

Screening of a λZAP human cerebellar library resulted in the isolation of 3 recombinant bacteriophage clones. None reacted with normal human serum. The phage clones were subcloned into pBluescript using the phage excision protocol. The resulting bacterial cDNA plasmids contained inserts of 2139 bp and sequence analysis demonstrated that all clones had identical inserts. Further studies were done using plasmid p8A which was derived from clone 8-3A1.

The cDNA sequence (SEQ ID NO:3, shown in FIG. 1) revealed an open reading frame (ORF) with two putative initiation AUG codons separated by one codon. The first of these, at nucleotide 272, is likely to be the translation initiatior codon as it most closely fits the Kozak consensus rule (Kozak, M., *Nuci. Acids Res.* 15:8125–8148 (1987)). The ORF extends until the first in-frame stop codon at nucleotide 1258 and encodes a protein of 330 amino acids (SEQ ID NO:4, FIG. 1) with a predicted molecular mass of 36.8 kDa. We called this gene product, Ma1. In addition to the ORF, the cDNA clone includes 5' non-coding sequence and a 3' polyadenylation signal (GenBank AF037364, shown in FIG. 1 as SEQ ID NO:3). A search of the EMBL/GenBank databases revealed that Ma1 cDNA nucleotides 272 to 546 had 97% identity with a human CpG island DNA genomic fragment (GenBank HS19A6R) (Cross, S.H. et al, *Nature Genet.* 6:236–244 (1994)), and nucleotides 794 to 1230 had 98% homology to cDNA clones derived from a human colon carcinoma cell line (GenBank AA314009) (Adams, M.D. et al., *Nature* 377:3–174 (1995)) and infant brain (GenBank H06341). These clones were derived during screenings for CpG islands and expressed sequence tags; no further characterizations have been published. A search of several databases for protein subsequence motifs revealed that the Ma1 protein contains several potential casein kinase II and protein kinase C phosphorylation sites but no other readily identifiable domains.

Sera From Patients With Paraneoplastic Symptoms Recognize Ma1 Fusion Protein

Using immunoblots of Ma1 fusion protein, the sera of all 4 patients with anti-Ma associated paraneoplastic symptoms reacted with a band of approximately 37 kDa. No reactivity was observed with sham protein (extracts of *E. coli* with parental plasmid without insert). None of the 337 control sera (patients with cancer but without paraneoplastic neurologic symptoms [cancer of the breast, colon, lung, or testicular germ cells], and patients with paraneoplastic neurologic symptoms [anti-Hu related, anti-Yo related]) reacted with Ma1.

To determine whether the antibodies against Ma1 correspond to the same antibodies that react with brain and testis, sections of these tissues and immunoblots of brain were incubated with anti-Ma sera that had been preabsorbed with Ma1 fusion protein or sham protein. Immunoabsorption with Ma1 protein, but not with sham protein, abrogated all the reactivity with testis and 80% of the reactivity with brain (only a few dot-like reactive granules remained positive in the nuclei of neurons). In addition, the serum preabsorbed with Ma1 no longer reacted with the 37 kDa neuronal protein, but remained reactive with the 40 kDa band, indicating that the 37 kDa protein corresponds to the cloned Ma1.

Expression of Ma1 mRNA in Human Tissues

Hybridization of an Ma1 specific oligonucleotide probe to Northern blots of mRNA from multiple human tissues showed that Ma1 mRNA was expressed by brain and testis, but not by placenta, lung, liver, spleen, thymus, prostate, ovary, small intestine, colon or peripheral blood leukocytes. The blots revealed a single band in both brain and testis of approximately 2.6 kilobases. The faint signal observed in heart, skeletal muscle, kidney and pancreas could represent either a very low level of Ma1 mRNA expression, or a trace of nervous tissue contained in these organs. In immunohistochemical and immunoblot assays (see above), these tissues did not react with anti-Ma serum, indicating no Ma1 protein expression.

Example 2

Identification of Cancer-Brain Antigen Using Serum Antibodies From Patients With Testicular Tumors and Paraneoplastic Limbic and Brainstem Encephalitis A. Materials and Methods Sera and Tissues The sera (or CSF when available) of 986 patients with histologically proven cancer that were sent to us for antineuronal antibody testing were used in the study. A total of 304 sera were used as controls; these controls included patients with cancer and paraneoplastic syndromes (45 PLE and tumors other than testicular cancer [13 anti-Hu positive]; 23 anti-Hu positive encephalomyelitis-sensory neuronopathy; 20 anti-Yo associated cerebellar degeneration; 5 Lambert-Eaton myasthenic syndrome, all positive for P/Q-type VGCC antibodies; 6 anti-Ri associated cerebellar ataxia and opsoclonus; and 9 myasthenia gravis and thymoma), patients with cancer but without paraneoplastic syndromes (44 testicular cancer; 10 colon cancer; 10 ovarian cancer; 21 breast cancer), and patients with miscellaneous disorders (41 multiple sclerosis; 35 systemic lupus erythematosus), and 24 normal individuals. All sera were kept frozen at −70° C.

Tumor tissues were provided by the referring physicians and by the Tumor Procurement Service at Memorial Sloan-Kettering Cancer Center. They included: 4 testicular tumors from patients with PLE-BE; 45 from patients without paraneoplastic syndromes (25 testicular germ cell tumors, 5 colon, 4 breast, 3 lung, 2 parotid gland and 6 SCLC), and 8 from patients with other paraneoplastic syndromes (4 SCLC, 3 ovary, 1 bladder). Normal human tissues and Wistar rats tissues were obtained as reported (Dalmau, J. et al., *Am. J. Pathol.* 141:881–6 (1992)), and kept at −70° C. Other samples from the same tissues were embedded in "Optimal Cutting Temperature" medium (OCT, Miles Inc, USA) and snap frozen in isopentane chilled by liquid nitrogen.

For Western blot analysis, tissues were homogenized in 0.1% Nonidet P-40 and protease inhibitors, as reported (Dalmau, J. et al., *Am. J. Pathol.* 141:881–6 (1992)).

Immunohistochemistry

Seven micron-thick frozen sections of rat and human tissues were fixed in 10% formalin, 100% methanol, or cold acetone (4° C.), and incubated with the patient's serum, IgG, or CSF using immunohistochemical methods previously reported (Dalmau, J. et al., *Am. J Pathol.* 141:881–6 (1992)).

To avoid reactivity with endogenous IgG, all immunohistochemical studies with human tissues utilized IgG purified from patients' sera and labeled with biotin. The same IgG was used for immune competition assays: two sera were considered as competing for the same epitopes when preincubation of the tissue with one serum abrogated the reactivity of the other serum's IgG.

Intrathecal Synthesis of Ta Antibodies

Intrathecal synthesis of Ta antibodies was calculated by the Schüller's formula (Schuuler, E., in *Trends in Neuroimmunology* (Marrosu, M. G., Cianchetti, C., and Tabolato, B., eds), Plenum Press, New York, 1990, pp. 3–12). A ratio of intrathecal antibody specific activity (ASA)/serum ASA>2 was considered a positive intrathecal synthesis.

Cloning, Isolation and Sequence Analysis of Ma2 cDNA

Using the serum of a patient with paraneoplastic brainstem dysfunction, a λZAP human cerebellar library (Stratagene, La Jolla, Calif.) was screened at a density of 5×104 pfu/150 mm plate. After 4 hours of growth at 42° C. plaques were overlaid with nitrocellulose filters soaked in 10 mM isopropyl b-D-thiogalactopyranoside (IPTG) and incubated for 12 hours at 37° C. Filters were removed, blocked with 1% bovine serum albumin in phosphate buffered saline (PBS), and incubated with the patient's serum (diluted 1:1000) for 2 hours at room temperature. Positive phage colonies were identified and purified by several rounds of antibody screening, followed by subcloning into pBluescript using the in vivo excision phage rescue protocol (Stratagene).

Double-stranded Ma2 cDNA was purified using the Qiagen plasmid midi-prep system (Qiagen, Santa Clarita, Calif.) and sequenced on both strands. Sequence analysis using internal oligonucleotide primers, as well as SK and KS primers was performed with an automated DNA sequencer (Applied Biosystems, model 377) using the dye terminator fluorescence method (Lee, L. G. et al, *Nuci. Acids Res.* 20:2471–2483 (1992)).

Western Blot Analysis

Fusion protein, *E. coli* protein, and proteins from human and rat tissues were obtained as previously described (Dalmau, J. et al., *Am. J. Pathol.* 141:881–6 (1992); Manley, G. T. et al., *Ann. Neurol.* 38:102–110 (1995)), resolved by 10% SDS-polyacrylamide gel electrophoresis, and transferred to nitrocellulose. Nitrocellulose strips were then incubated with the patients sera (diluted 1:1,000) and the reactivity demonstrated by an enhanced chemiluminescence method (Amersham, Arlington, Ill.).

Northern Blot Analysis

Sequence specific oligonucleotide probes were end-labeled with [g-$^{32}$P] ATP using T4 polynucleotide kinase, and purified over a G-25 sephadex column. As probe for Ma2, the following oligonucleotide was used: 5'-GGGAATGGCCGAGACATC-3' (SEQ ID NO:5) (cDNA base pairs 234–217), and as probe for β-actin, the following oligonucleotide was used: 5'-GTCTTTGCGGATGTCCACG-3' (SEQ ID NO:2). Probes (1×10$^7$ cpm/mL) were hybridized to "Human Multiple Tissue Northern Blots I and II" (Clontech, Palo Alto, Calif.) overnight at 42° C. in Rapid Hyb buffer (Amersham). Blots were washed for 15 minutes at RT in 5×SSC (20X= NaCl 3M and Na$_3$Citrate 0.3M, pH 7.0), 0.1% SDS; at 42° C. in 1×SSC, 0.1% SDS; and at 42° C. in 0.1×SSC, 0.1% SDS. After hybridization with the Ma2 probe, blots were stripped by boiling in 0.5% SDS for 10 minutes and hybridized with β-actin probe. For visualization, blots were exposed to XAR film for 72 hours at −80° C.

B. Results

Patients

Among 986 patients with several types of cancer whose sera were examined for onconeuronal antibodies, 20 had testicular cancer and diverse paraneoplastic syndromes. Ten of these 20 patients harbored similar antineuronal antibodies, termed Ta (see below), and all 10 suffered from PLE, BE, or both (Table 2). Only 1 of 9 patients with PLE did not harbor Ta antibodies.

TABLE 2

Paraneoplastic Symptoms in 20 Patients with Testicular Cancer

|  | Ta antibodies (+) | Ta antibodies (−) |
|---|---|---|
| Limbic encephalitis* | 8 | 1 |
| Brainstem** | 2 | 2 |
| Cerebellum | 0 | 1 |
| Basal ganglia dysfunction | 0 | 1 |
| Sensory neuropathy | 0 | 3 |
| Optic neuritis-myelitis | 0 | 1 |
| Motor neuron syndrome | 0 | 1 |

*Two (2) patients also had brainstem dysfunction, and another 2 had severe hypothalamic involvement.
**Prominent brainstem dysfunction.

The clinical features of the patients with Ta antibodies are shown in Table 3. Eight patients had PLE (2 associated with BE); symptoms included, severe memory loss n=5 patients), seizures (n=6), and hypothalamic-diencephalic dysfunction (2 hyperthermia, 1 hypersomnia, 1 pathological increase of weight, 1 pituitary hormonal deficits). Two additional patients had prominent BE with marked eye movement abnormalities. Mild cerebellar symptoms were identified in 3 patients, all with conspicuous signs of BE.

TABLE 3

Clinical Features of 10 Patients with Paraneoplastic Symptoms Associated with Ta Antibodies

| # | Sex | Age | First Symptoms | Syndrome | CNS Diagnostic Tests | Tumor Diagnosis | Tumor Type | Treatment | Status |
|---|---|---|---|---|---|---|---|---|---|
| 1 | M | 28 | Resting tremor, slow mentation, anxiety, irritability, depression, dystonia, seizures, memory problems | Basal ganglia, PLE | CT: normal *CSF: abnormal | 1 year prior to the ND | NSGCT | orchiectomy, plasma exchange, corticosteroids | Neurology: stable Tumor: NED (3 years) |
| 2 | M | 45 | Depression, memory changes, seizures, weight gain (20 lbs) | PLE | **MRI: abnormal CSF: normal Brain biopsy: PLE | 3 years after the ND | NSGCT | orchiectomy, chemotherapy | Neurology stable; Tumor: NED (9 years) |

TABLE 3-continued

Clinical Features of 10 Patients with Paraneoplastic Symptoms Associated with Ta Antibodies

| # | Sex | Age | First Symptoms | Syndrome | CNS Diagnostic Tests | Tumor Diagnosis | Tumor Type | Treatment | Status |
|---|-----|-----|----------------|----------|---------------------|-----------------|------------|-----------|--------|
| 3 | M | 26 | Memory loss, seizures | PLE | MRI: abnormal CSF: abnormal Brain biopsy: PLE | 9 months after the ND | NSGCT | orchiectomy, chemotherapy | Neurology: remission; Tumor: NED (3 years) |
| 4 | M | 37 | Severe memory loss, mild brainstem signs, hypersomnia | PLE, BE | MRI: abnormal CSF: abnormal | 2 months after the ND | Seminoma | orchiectomy, chemotherapy, corticosteroids | Neurology: remission; Tumor: metastases |
| 5 | M | 22 | Seizures (left facial twitching and abnormal taste in mouth) | PLE | MRI: abnormal CSF: abnormal, Brain biopsy: PLE | 6 months after the ND | MGCT | orchiectomy, chemotherapy, carbamazepine | Died of neurological deterioration |
| 6 | M | 28 | Hallucinations, seizures (deja vu), memory loss, hyperthermia | PLE, cerebellar | MRI: abnormal CSF: abnormal | 6 months after the ND | MGCT | orchiectomy, chemotherapy | Died of complications of chemotherapy |
| 7 | M | 45 | Ataxia, dysarthria | BE, cerebellar | MRI: normal CSF: normal | 6 months after the ND | Seminoma | orchiectomy, radiation, carbamazepine | Neurology: partial improvement Tumor: NED (3 years) |
| 8 | M | 28 | Visual/auditory hallucinations, confusion, eye motility disfunction, memory loss, hyperthermia | PLE, BE | MRI: abnormal CSF: abnormal Brain biopsy: PLE | 7 months prior to the ND | NSGCT | orchiectomy, steroids, IV Ig | Neurology: deterioration; Tumor: NED (9 months) |
| 9 | M | 32 | Diplopia, dysarthria, oscillopsia | BE, cerebellar | MRI: normal CSF: normal | 12 months after the ND | Seminoma | orchiectomy | Neurology: stable Tumor: NED (4 months) |
| 10 | M | 38 | Lethargy, loss of libido, diabetes insipidus, hypothyroidism, urinary incontinence, mutism, hypersomnia, Decreased voluntary movements | PLE, diencephalon, hyopthalamus | MRI: abnormal CSF: abnormal | 5 months after the ND | Seminoma | orchiectomy, dexamphetamine, IV Ig, corticosteroids | Neurology: mild improvement Tumor: NED (3 months) |

ND: Neurologic disease;
NSGCT: Non-seminomatous germ-cell tumor;
MGCT: mixed germ-cell tumor;
PLE: paraneoplastic limbic encephalitis;
BE: brainstem encephalitis;
IV Ig: Intravenous immunoglobulin;
NED: no evidence of disease (cancer).
(*)CSF: abnormal, indicates elevated proteins, pleocytosis, or both. In all patients, the CSF cytology was negative for cancer cells.
(**): MRI of the head: abnormalities on T2-weighted sequences involving one or both temporal lobes (n = 7), suprasellar-diencephalic regio (n = 3), and uptake of gadolinium in temporal or diencephalic regions (n = 3).

Neurological symptoms developed before the tumor diagnosis in 8 patients (median 6 months, range 2–36 months); in the other 2 the tumor diagnosis preceded the neurological disorder (7 and 12 months). Head MRI was abnormal in 7 PLE patients; the typical findings included a bright signal in the medial aspect of the temporal loves, and sometimes the diencephalon. Four patients underwent brain biopsy; all showed inflammatory infiltrates, gliosis, and neuronal degeneration. More intense signal in a right temporal lobe corresponded to local edema after a brain biopsy, which showed perivascular inflammatory infiltrates and multiple perineuronal infiltrates of T cells Two patients had relapsing and remitting neurological symptoms: one was reported elsewhere (Burton, G. V. et al., Cancer 62:2248–2251 (1988)), the other had symptoms for 12 months until the detection of serum Ta antibodies established the diagnosis of paraneoplastic BE and lead to the discovery of the tumor. All patients had testicular tumors (4 seminomas and 6 non-seminomatous germ cell tumors). At the time of tumor diagnosis, 4 patients had systemic metastasis.

All 10 patients underwent orchiectomy, 5 received chemotherapy, and 1 radiation therapy. The neurologic disease was treated with steroids (n=4), plasma exchange (n=2), and intravenous immunoglobulin (IVIG, n=1). Only one patient treated with IVIG and steroids improved. Overall, 5 patients improved neurologically (2 with total remission), 2 remained stable, 1 deteriorated, and 2 are dead (one from complications of chemotherapy; the other from the neurologic disease).

Detection of Ta Antibodies

Using immunoblots of purified human neurons, the sera of the 10 patients (and CSF available from 6) reacted with a 40 kDa protein. The distribution and pattern of reactivity was examined by immunohistochemistry of human and rat tissues using several fixatives and different tissue processing. All sera and CSF showed a similar brain-specific reactivity. The most intense immunolabeling was obtained with frozen tissue and acetone or methanol-acetone fixation. Using these conditions most neurons of the central nervous system showed discrete subnuclear and cytoplasmic reactive structures; the reactivity appeared concentrated in the nucleoli and perikaryon. With formalin fixed tissue, only subgroups of neurons of the amygdaloid complex, large neurons of the brainstem, and the dentate nucleus of the cerebellum remained positive. Preincubation of tissues with any of 8 sera abolished the reactivity of the IgG isolated from the other 2 sera, suggesting that all sera had similar epitope specificity.

The reactivity defined by these immunoblot and immunohistochemical techniques was called "Ta" (after the first two letters of the index patient's name). Ta antibodies were not identified in 304 control sera, including patients with cancer and paraneoplastic syndromes (45 PLE and tumors other than testicular cancer [13 anti-Hu positive]; 23 anti-Hu positive encephalomyelitis-sensory neuronopathy; 20 anti-Yo associated cerebellar degeneration; 5 Lambert-Eaton myasthenic syndrome, all positive for P/Q-type VGCC antibodies; 6 anti-Ri associated cerebellar ataxia and opsoclonus; and 9 myasthenia gravis and thymoma), patients with cancer but without paraneoplastic syndromes (44 testicular cancer; 10 colon cancer; 10 ovarian cancer; 21 breast cancer), and patients with miscellaneous disorders (41 multiple sclerosis; 35 systemic lupus erythematosus), and 24 normal individuals (anti-Hu: see Szabo, A. et al., *Cell* 67:325–333 (1991); anti-Yo: see Peterson, K. et al., *Neurology* 42:1931–37 (1992); anti-Ri: see Luque, F. A. et al., *Ann. Neurol.* 29:241–251 (1991)).

C. Cloning and Characterization of Ma2, the Antigen Recognized By Ta Antibodies Cloning of Ma2

The screening of a λZAP human cerebellar library with the serum of a patient resulted in the isolation of a positive clone, which was recovered by subcloning in pBluescript. The resulting plasmid (p561A) contained an insert of 614 bp. Sequence analysis revealed the presence of an incomplete open reading frame of 195 amino acids, with a predicted molecular mass of 21.9 kDa (GenBank AF037365, shown in FIG. 2 as SEQ ID NO:6). The nucleic acid sequence (SEQ ID NO:6) and predicted amino acid sequence (SEQ ID NO:7) are shown in FIG. 2. A stop codon at 586 bp is almost immediately followed by an apparent polyadenylation signal. The methionines at amino acids 12 and 21 do not closely fit the Kozak consensus rule for initiation codons making it unlikely that the clone is complete at the 5' end. The protein expressed by this cDNA was called, Ma2.

Figure 3A:
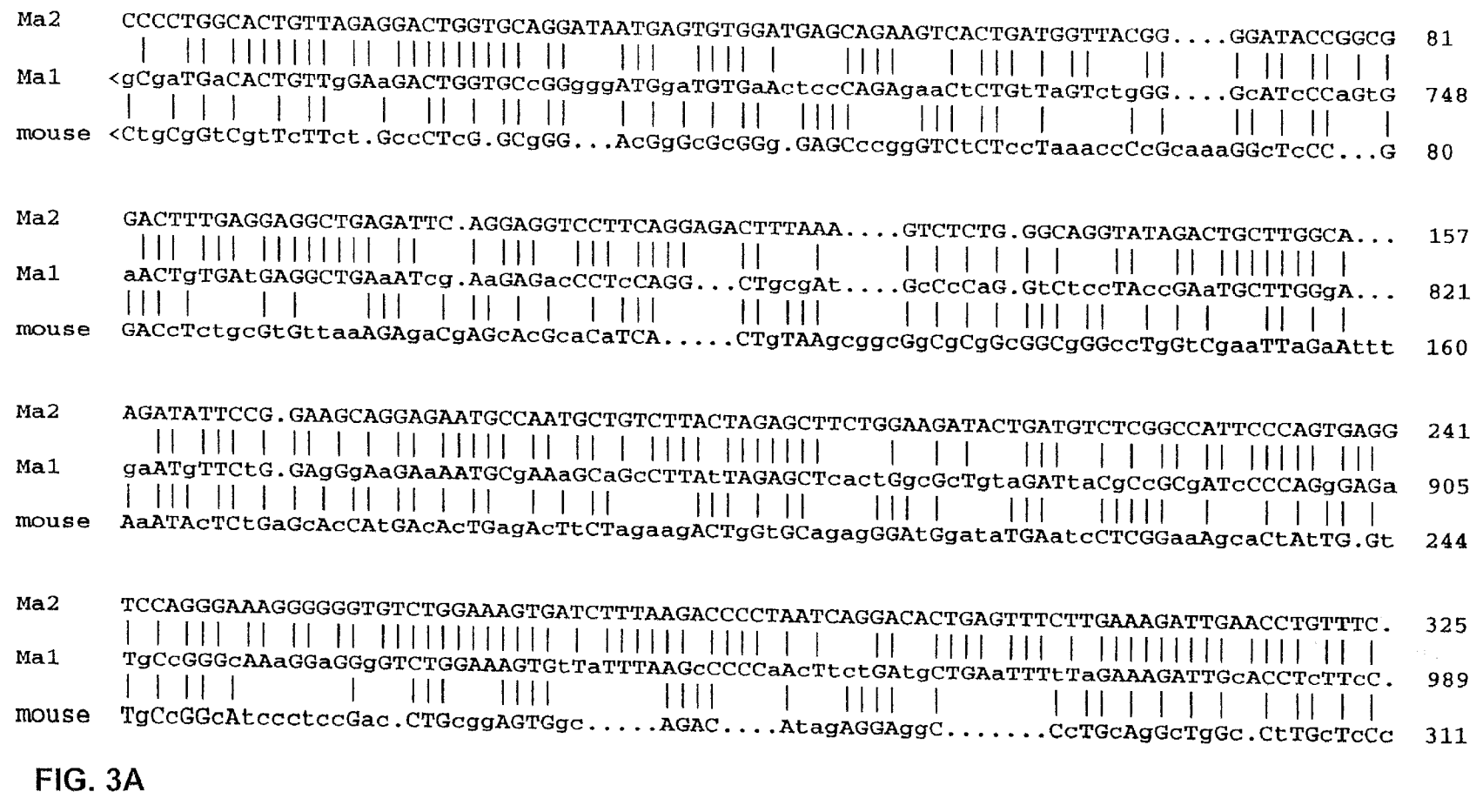

It was found that the cDNA sequence of Ma2 is partially homologous to Ma1 (FIGS. 3A and 3B), the paraneoplastic antigen expressed in brain and testis (see Example 1). A search of the GenBank databases revealed that the Ma2 cDNA had 84% homology to a human cDNA clone derived from RNA extracted from demyelinating lesions of a patient with multiple sclerosis (GenBank N47784). Further analysis showed that the area of highest homology (95%) is within the putative protein coding region of Ma2 and in fact, accounting for sequencing errors, the 2 clones are likely identical in this region. The N47784 clone has a potential ORF that extends beyond the Ma2 stop codon. In addition, Ma2 was found to have 60% homology to a cDNA clone isolated from adult mouse testis (GenBank 918103).

Patients With Testicular Cancer and PLE-BE Harbor Serum Antibodies Against Ma2 and Have an Intrathecal Synthesis of These Antibodies Using immunoblots of Ma2 fusion protein, all sera and CSF from patients with Ta antibodies reacted with a band of approximately 32 kDa. No reactivity was obtained with immunoblots of sham protein (*E. coli* with parental plasmid without insert). None of 304 control sera reacted with Ma2.

To determine whether Ma2 corresponds to the 40 kDa neuronal protein identified by Ta antibodies, immunoblots of neuronal proteins were incubated with anti-Ta sera preabsorbed with Ma2. Preabsorption with Ma2, but not with sham protein, abrogated the serum reactivity with the 40 kDa neuronal protein, suggesting that this protein is Ma2.

The ratio of intrathecal ASA/serum ASA of Ta antibodies was 0.74, 4.4, 6.2, 16.9, and 23.5, consistent with a positive intrathecal synthesis (>2) in 4 of 5 patients.

Ma2 is Expressed By Normal Brain and By the Tumor of Patients With PLE-BE

Northern blot analysis of mRNA extracted from multiple human tissues showed that Ma2 mRNA is expressed by brain, but not by placenta, lung, liver, spleen, thymus, prostate, ovary, testis, small intestine, colon or peripheral blood leukocytes. The Northern blots revealed a single transcript expressed in brain of approximately 6,500 kilobases. Immunohistochemical and Western blot analysis of the same tissues, using biotinylated anti-Ta IgG as a probe, showed that only brain expresses Ma2 reactivity.

The tumors of 4 patients with PLE-BE and Ta antibodies were available in formalin-fixed, paraffin-embedded blocks. After tissue deparaffination and antigen retrieval, all 4 tumors showed reactivity with anti-Ta IgG. No reactivity was observed when the IgG had been preabsorbed with Ma2 protein. Results were similar with sections or fat hippocampus. No Ma2 reactivity was expressed by 53 diverse tumors (including 25 testicular cancers) from patients without paraneoplastic syndromes or with other paraneoplastic disorders.

D. Ma1 and Ma2 are Targets of Immunological Responses Associated With Different Profiles of Neurologic Symptoms and Tumors Because of the sequence homology between Ma1 and Ma2, it was examined whether anti-Ta and anti-Ma sera react with both proteins. These studies showed that all anti-Ta sera react exclusively with Ma2, but the anti-Ma sera recognize both Ma proteins. Preabsorption of anti-Ma sera with any of these proteins did not abrogate the reactivity with the other one, indicating that the epitopes in Ma1 and Ma2 are different. In addition, preincubation of rat brain sections and immunoblots of neuronal proteins and Ma2 with any anti-Ma serum decreased, but did not abolish, the reactivity with anti-Ta IgG suggesting that some, but not all, Ma2 epitopes are recognized by both types of sera. The clinical-immunological associations derived from these studies are summarized in FIG. 4.

Example 3

Identification of Ma3, Ma4 and Ma5

Screening of a human brainstem cDNA library, using the same techniques as described above for isolation of Ma1 and Ma2 from the cerebellar library, resulted in the isolation of 3 additional clones with homology to Ma3 and Ma2; these were named Ma3, Ma4 and Ma5. Ma3 is 833 nucleotides long, encoding a fusion protein of 21 kilodaltons. Ma4 is 1574 nucleotides long, encoding a fusion protein of 36 kilodaltons. Ma5 is 2248 nucleotides long, encoding a fusion protein of 56 kilodaltons. The fusion proteins are those proteins expressed by thecDNA clones in pbluescript, which is a fusion between the clone and the 5'-end of the β-galactosidase gene. The cDNA for Ma3, Ma4 and Ma5 have been deposited in Genbank as AF083114 (Ma3, shown in FIG. 5 as SEQ ID NO:8), AF083115 (Ma4, shown in FIGS. 6A–6B as SEQ ID NO:10), and AF083116 (Ma5, shown in FIGS. 7A–7B as SEQ ID NO:12). The putative encoded polypeptides for Ma3, Ma4 and Ma5 are shown in FIGS. 5 (SEQ ID NO:9), 6A–6B (SEQ ID NO:11) and 7A–7B (SEQ ID NO:13), respectively.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of diagnosing a neurologic disorder associated with the presence of a neoplasm in an individual, comprising assessing a test sample from the individual for the presence of antibodies to a Ma family polypeptide, wherein the Ma family polypeptide is selected from the group consisting of:
   a) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
   b) Ma1 (SEQ ID NO:4),
   c) Ma2 (SEQ ID NO:7),
   d) Ma3 (SEQ ID NO:9),
   e) Ma4 (SEQ ID NO:11), and
   f) Ma5 (SEQ ID NO:13),
wherein the presence of antibodies to a Ma family polypeptide is indicative of the presence of the neurologic disorder associated with the presence of a neoplasm.

2. The method of claim 1, wherein the Ma family polypeptide is Ma1.

3. The method of claim 1, wherein the Ma family polypeptide is Ma2.

4. The method of claim 3, wherein the neurologic disorder associated with the presence of a neoplasm is paraneoplastic limbic encephalitis or brainstem encephalitis, or both paraneoplastic limbic encephalitis and brainstem encephalitis.

5. A method of diagnosing a neurologic disorder associated with the presence of a neoplasm in an individual, comprising assessing a test sample from the individual for the absence of antibodies to a Ma family polypeptide wherein the Ma family polypeptide is selected from the group consisting of:
   a) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
   b) Ma1 (SEQ ID NO:4),
   c) Ma2 (SEQ ID NO:7),
   d) Ma3 (SEQ ID NO:9),
   e) Ma4 (SEQ ID NO:11), and
   f) Ma5 (SEQ ID NO:13),
wherein the absence of antibodies to a Ma family polypeptide is indicative of the absence of the neurologic disorder associated with the presence of a neoplasm.

6. The method of claim 5, wherein the Ma family polypeptide is Ma1.

7. The method of claim 5, wherein the Ma family polypeptide is Ma2.

8. The method of claim 7, wherein the neurologic disorder associated with the presence of a neoplasm is paraneoplastic limbic encephalitis or brainstem encephalitis, or both paraneoplastic limbic encephalitis and brainstem encephalitis.

9. A method of diagnosing a neurologic disorder associated with the presence of a neoplasm in an individual, comprising the steps of:
   a) contacting a test sample from the individual with a Ma family polypeptide sample, wherein the Ma family polypeptide is selected from the group consisting of:
      1) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
      2) Ma1 (SEQ ID NO:4),
      3) Ma2 (SEQ ID NO:7),
      4) Ma3 (SEQ ID NO:9),
      5) Ma4 (SEQ ID NO:11), and
      6) Ma5 (SEQ ID NO:13),
   under conditions that allow antibodies, of present, to blind to Ma family, polypeptide, thereby generating a compacted sample; and b) comparing the amount of anti-Ma family polypeptide antibody in the contacted sample with a reference amount, wherein an amount of anti-Ma family polypeptide antibodies in the contacted sample that is equal to, or greater than, the reference amount, is indicative of the presence of the neurologic disorder associated with the presence of a neoplasm.

10. The method of claim 9, wherein the Ma family polypeptide sample comprises Ma1.

11. The method of claim 9, wherein the Ma family polypeptide sample comprises Ma1.

12. The method of claim 9, wherein the Ma family polypeptide sample comprises Ma1 and Ma2.

13. The method of claim 9, wherein the test sample comprises a sample selected from the group consisting of: blood, serum, cerebrospinal fluid, urine, nasal secretion, and saliva.

14. The method of claim 9, wherein the test sample comprises antibodies isolated from a sample of bodily fluid or tissue.

15. A method of diagnosing a neurologic disorder associated with the presence of a neoplasm in an individual, comprising the steps of:
   a) contacting a test sample from the individual with a Ma family polypeptide sample, wherein the Ma family polypeptide is selected from the group consisting of:
      1) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
      2) Ma1 (SEQ ID NO:4),
      3) Ma2 (SEQ ID NO:7),
      4) Ma3 (SEQ ID NO:9),
      5) Ma4 (SEQ ID NO:11), and
      6) Ma5 (SEQ ID NO:13),
      under conditions that allow antibodies, if present, to bind to Ma family polypeptide, thereby generating a contacted sample; and
   b) comparing the amount of anti-Ma family polypeptide antibody in the contacted sample with a reference amount, wherein an amount of anti-Ma family polypeptide antibodies in the contacted sample that is less than the reference amount is indicative of the absence of the neurologic disorder associated with the presence of a neoplasm.

16. The method of claim 15, wherein the Ma family polypeptide sample comprises Ma1.

17. The method of claim 15, wherein the Ma family polypeptide sample comprises Ma2.

18. The method of claim 15, wherein the Ma family polypeptide sample comprises Ma1 and Ma2.

19. The method of claim 15, wherein the test sample comprises a sample selected from the group consisting of: blood, serum, cerebrospinal fluid, urine, nasal secretion, and saliva.

20. The method of claim 15, wherein the test sample comprises antibodies isolated from a sample of bodily fluid or tissue.

21. A method of diagnosing a neurologic disorder associated with the presence of a neoplasm in an individual, comprising the steps of:
   a) contacting a test sample from the individual with a Ma family polypeptide sample, wherein the Ma family polypeptide is selected from the group consisting of:
      1) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
      2) Ma1 (SEQ ID NO:4),
      3) Ma2 (SEQ ID NO:7),
      4) Ma3 (SEQ ID NO:9),
      5) Ma4 (SEQ ID NO:11), and
      6) Ma5 (SEQ ID NO:13),
      under conditions that allow antibodies, if present, to bind to Ma family polypeptide, thereby generating a contacted sample;
   b) determining the amount of anti-Ma family polypeptide antibody in the contacted sample; and
   c) comparing the amount of anti-Ma family polypeptide antibody in the contacted sample with the amount of anti-Ma family polypeptide antibody in at least one comparable negative control sample, wherein an amount of anti-Ma family polypeptide antibody in the contacted sample flat is significantly greater than an amount of anti-Ma family polypeptide antibody in a comparable negative control sample is indicative of the presence of the neurologic disorder associated with the presence of a neoplasm.

22. The method of claim 21, wherein the Ma family polypeptide sample comprises Ma1.

23. The method of claim 21, wherein the Ma family polypeptide sample comprises Ma2.

24. The method of claim 21, wherein the Ma family polypeptide sample comprises Ma1 and Ma2.

25. The method of claim 21, wherein the test sample comprises a sample selected from the group consisting of: blood, serum, cerebrospinal fluid, urine, nasal secretion, and saliva.

26. The method of claim 21, wherein the test sample comprises antibodies isolated from a sample of bodily fluid or tissue.

27. A method or diagnosing a neurologic disorder associated with the presence of a neoplasm in an individual, comprising the steps of:
   a) contacting a test sample from the individual with a Ma family polypeptide sample, wherein the Ma family polypeptide is selected from the group consisting of:
      1) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
      2) Ma1 (SEQ ID NO:4),
      3) Ma2 (SEQ ID NO:7),
      4) Ma3 (SEQ I) NO:9),
      5) Ma4 (SEQ ID NO:11), and
      6) Ma5 (SEQ ID NO:13),
      under conditions that allow antibodies, if present, to bind to Ma Family polypeptide thereby generating a contacted sample;
   b) determining the amount of anti-Ma family polypeptide antibody in the contacted sample; and
   c) comparing the amount of anti-Ma family polypeptide antibody in the contacted sample with the amount of anti-Ma family polypeptide antibody in at least one comparable negative control sample, wherein an amount of anti-Ma family polypeptide antibody in the contacted sample that is not significantly greater than an amount of anti-Ma family polypeptide antibody in a comparable negative control sample is indicative of the absence of the neurologic disorder associated with the presence of a neoplasm.

28. The method of claim 27, wherein the Ma family polypeptide sample comprises Ma1.

29. The method of claim 27 wherein the Ma family polypeptide sample comprises Ma2.

30. The method of claim 27, wherein the Ma family polypeptide sample comprises Ma1 and Ma2.

31. The method of claim 27, wherein the test sample comprises a sample selected from the group consisting of: blood, serum, cerebrospinal fluid, urine, nasal secretion, and saliva.

32. The method of claim 27, wherein the test sample comprises antibodies isolated from a sample of bodily fluid or tissue.

33. A method of diagnosing a neoplasm in an individual, comprising assessing a test sample from the individual for the presence of antibodies to a Ma family polypeptide, wherein the Ma family polypeptide is selected from the group consisting of:
  a) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO:13),
  b) Ma1 (SEQ ID NO:4),
  c) Ma2 (SEQ ID NO:7),
  d) Ma3 (SEQ ID NO:9),
  e) Ma4 (SEQ ID NO:11), and
  f) Ma5 (SEQ ID NO:13),
wherein the presence of antibodies to a Ma family polypeptide is indicative of the presence of a neoplasm.

34. The method of claim 33, wherein the Ma family polypeptide is Ma1.

35. The method of claim 34, wherein the neoplasm is selected from the group consisting of: breast cancer, colon cancer, parotid gland cancer, lung cancer, testicular cancer and germ-cell tumors.

36. The method of claim 33, wherein the Ma family polypeptide is Ma2.

37. The method of claim 36, wherein the neoplasm is testicular cancer or a germ cell tumor, or both testicular cancer and a germ cell tumor.

38. A method of diagnosing a neoplasm in an individual, comprising assessing a test sample from the individual for the presence or absence of antibodies to a Ma family polypeptide, wherein the Ma family polypeptide is selected from the group consisting of:
  a) a polypeptide that is expressed by the brain or testis, or both brain and testis, and that is recognized by antibodies that specifically bind to one or more polypeptides selected from the group consisting of: Ma1 (SEQ ID NO:4), Ma2 (SEQ ID NO;7), Ma3 (SEQ ID NO:9), Ma4 (SEQ ID NO:11) and Ma5 (SEQ ID NO:13),
  b) Ma1 (SEQ ID NO:4),
  a) Ma2 (SEQ ID NO:7),
  d) Ma3 (SEQ ID NO:9),
  e) Ma4 (SEQ ID NO:11), and
  f) Ma5 (SEQ ID NO:13),
wherein the absence of antibodies to a Ma family polypeptide is indicative of the absence of a neoplasm.

39. The method of claim 38, wherein the Ma family polypeptide is Ma1.

40. The method of claim 39, wherein the neoplasm is selected from the group consisting of: breast cancer, colon cancer, parotid gland cancer, lung cancer, testicular cancer and germ-cell tumors.

41. The method of claim 38, wherein the Ma family polypeptide is Ma2.

42. The method of claim 41, wherein the neoplasm is testicular cancer or a germ cell tumor, or both testicular cancer and a germ cell tumor.

43. A kit for use in diagnosis of a neurologic disorder associated with the presence of a neoplasm, comprising
  a) a Ma family polypeptide sample, wherein the Ma family polypeptide is selected from the group consisting of:
    1) a polypeptide that is expressed by the brain or testis, or both brain and tests, and that is recognized by antibodies that specifically bind to one or more polypeptides selected from the group consisting of: Ma1 (SEQ ID NO:4), Ma2 (SEQ ID NO:7), Ma3 (SEQ ID NO:9), Ma4 (SEQ ID NO:11) and Ma5 (SEQ ID NO, 13),
    2) Ma1 (SEQ ID NO:4),
    3) Ma2 (SEQ ID NO:7),
    4) Ma3 (SEQ ID NO:9),
    5) Ma4 (SEQ ID NO:11), and
    6) Ma5 (SEQ ID NO:13), b) a detector antibody that binds to anti-Ma family polypeptide antibody.

44. The kit of claim 43, wherein the Ma family polypeptide sample comprises Ma1.

45. The kit of claim 43, wherein the Ma family polypeptide sample comprises Ma2.

46. The kit of claim 43, wherein the Ma family polypeptide sample comprises Ma1 and Ma2.

* * * * *

UNITED STATES PATENT AND TRADEMARK OFFICE
CERTIFICATE OF CORRECTION

PATENT NO. : 6,387,639 B1
DATED : May 14, 2002
INVENTOR(S) : Jerome B. Posner, Josep O. Dalmau and Myrna R. Rosenfeld It is certified that error appears in the above-identified patent and that said Letters Patent is hereby corrected as shown below:

Column 50,
Line 67, delete "blind" and insert -- bind --.

Column 51,
Line 11, delete "Ma1" and insert -- Ma2 --.

Column 54,
Line 44, insert a line break after "(SEQ ID NO:13)," beginning "b)" on line 45, aligned with "a)" in line 30.

Signed and Sealed this

Twenty-fifth Day of June, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

Page 1 of 1

PATENT NO.       : 6,387,639 B1
APPLICATION NO.  : 09/189527
DATED            : May 14, 2002
INVENTOR(S)      : Samuel Danishefsky It is certified that error appears in the above-identified patent and that said Letters Patent is hereby corrected as shown below:

In the Specification

In column 1, beginning at line 21 and ending at line 24, please delete:

"The invention was supported, in whole or in part, by grant NS-26064 from the National Institutes of health, and grant 08748 from the National Cancer Institute. The United States Government has certain rights in the invention."

and insert:

--This invention was made with government support under grant numbers NS026064 and CA008748 awarded by National Institutes of Health. The government has certain rights in the invention.--

Signed and Sealed this
Eighth Day of March, 2016

Michelle K. Lee
*Director of the United States Patent and Trademark Office*

SEQUENCE LISTING

<160> NUMBER OF SEQ ID NOS: 14

<210> SEQ ID NO 1
<211> LENGTH: 18
<212> TYPE: DNA
<213> ORGANISM: homo sapiens

<400> SEQUENCE: 1
gaaacccaag gacacggg                                                      18

<210> SEQ ID NO 2
<211> LENGTH: 19
<212> TYPE: DNA
<213> ORGANISM: homo sapiens

<400> SEQUENCE: 2
gtctttgcgg atgtccacg                                                     19

<210> SEQ ID NO 3
<211> LENGTH: 2139
<212> TYPE: DNA
<213> ORGANISM: homo sapiens
<220> FEATURE:
<221> NAME/KEY: CDS
<222> LOCATION: (272)...(1258)
<221> NAME/KEY: misc_feature
<222> LOCATION: (1)...(2139)
<223> OTHER INFORMATION: n = A,T,C or G

<400> SEQUENCE: 3

```
cgaggagcga cggccggacc cagacccaga cgcaagatgg cgacggccgc gtgactgcct         60
cagcgtcccc gagctcggct ccgagtgcac ctacggactg actgtggggg cagagaaggg        120
cgagatcagg actctgtctt tgttaatcgt gactgcatga aggtcgcctc cctcgggcct        180
acttggtggg agtgtctggt attgttctaa ggccaggagc acgtgagcc acagtctgtt         240 ggtagaattt ggcgtcttga tagttgagaa a atg gcg atg aca ctg ttg gaa          292
                                   Met Ala Met Thr Leu Leu Glu
                                     1               5 gac tgg tgc cgg ggg atg gat gtg aac tcc cag aga act ctg tta gtc         340
Asp Trp Cys Arg Gly Met Asp Val Asn Ser Gln Arg Thr Leu Leu Val
       10                  15                  20 tgg ggc atc cca gtg aac tgt gat gag gct gaa atc gaa gag acc ctc         388
Trp Gly Ile Pro Val Asn Cys Asp Glu Ala Glu Ile Glu Glu Thr Leu
   25                  30                  35 cag gct gcg atg ccc cag gtc tcc tac cga atg ctt ggg aga atg ttc         436
Gln Ala Ala Met Pro Gln Val Ser Tyr Arg Met Leu Gly Arg Met Phe
40                  45                  50                  55 tgg agg gaa gaa aat gcg aaa gca gcc tta tta gag ctc act ggc gct         484
Trp Arg Glu Glu Asn Ala Lys Ala Ala Leu Leu Glu Leu Thr Gly Ala
                60                  65                  70 gta gat tac gcc gcg atc ccc agg gag atg ccg ggc aaa gga ggg gtc         532
Val Asp Tyr Ala Ala Ile Pro Arg Glu Met Pro Gly Lys Gly Gly Val
            75                  80                  85 tgg aaa gtg tta ttt aag ccc cca act tct gat gct gaa ttt tta gaa         580
Trp Lys Val Leu Phe Lys Pro Pro Thr Ser Asp Ala Glu Phe Leu Glu
        90                  95                 100 aga ttg cac ctc ttc cta gct aga gag ggg tgg acc gtg caa gat gtt         628
Arg Leu His Leu Phe Leu Ala Arg Glu Gly Trp Thr Val Gln Asp Val
    105                 110                 115 gcc cgt gtc ctt ggg ttt cag aac cct act ccg acc ccg ggc cca gag         676
```

-continued

```
Ala Arg Val Leu Gly Phe Gln Asn Pro Thr Pro Thr Pro Gly Pro Glu
120                 125                 130                 135 atg cca gca gag atg cta aac tat att ttg gat aat gtt att cag cct       724
Met Pro Ala Glu Met Leu Asn Tyr Ile Leu Asp Asn Val Ile Gln Pro
                140                 145                 150 ctt gtt gag tcc ata tgg tac aag agg ctg aca ctt ttc tcg ggg aag       772
Leu Val Glu Ser Ile Trp Tyr Lys Arg Leu Thr Leu Phe Ser Gly Lys
            155                 160                 165 gga cat ccc agg gcc tgg aga gga aac ttt gat ccc tgg ctg gag cac       820
Gly His Pro Arg Ala Trp Arg Gly Asn Phe Asp Pro Trp Leu Glu His
        170                 175                 180 act aat gag gtc cta gag gag tgg cag gtg tcc gat gta gaa aag agg       868
Thr Asn Glu Val Leu Glu Glu Trp Gln Val Ser Asp Val Glu Lys Arg
    185                 190                 195 cgg cgg ttg atg gag agt ctt aga ggc ccc gcc gct gat gtt att cgc       916
Arg Arg Leu Met Glu Ser Leu Arg Gly Pro Ala Ala Asp Val Ile Arg
200                 205                 210                 215 atc ctt aag tcc aac aac ccc gcg ata acc act gcc gaa tgc ctg aag       964
Ile Leu Lys Ser Asn Asn Pro Ala Ile Thr Thr Ala Glu Cys Leu Lys
                220                 225                 230 gcg ctt gag cag gtg ttt ggg agc gtt gag agc tct agg gat gcc cag      1012
Ala Leu Glu Gln Val Phe Gly Ser Val Glu Ser Ser Arg Asp Ala Gln
            235                 240                 245 atc aaa ttt ctg aac act tat cag aac ccg gga gaa aaa ttg tct gct      1060
Ile Lys Phe Leu Asn Thr Tyr Gln Asn Pro Gly Glu Lys Leu Ser Ala
        250                 255                 260 tat gtc att cgt ctg gag cct ctg cta cag aag gtg gta gag aag ggg      1108
Tyr Val Ile Arg Leu Glu Pro Leu Leu Gln Lys Val Val Glu Lys Gly
    265                 270                 275 gcc att gat aaa gat aat gtg aac cag gcc cgc cta gag cag gtc att      1156
Ala Ile Asp Lys Asp Asn Val Asn Gln Ala Arg Leu Glu Gln Val Ile
280                 285                 290                 295 gcc ggg gcc aac cac agc ggg gcc atc cga agg cag ctg tgg ctt acc      1204
Ala Gly Ala Asn His Ser Gly Ala Ile Arg Arg Gln Leu Trp Leu Thr
                300                 305                 310 ggg gct ggg gaa ggg cca ggc ccc aaa cct ctt tca gtt gct ggt gca      1252
Gly Ala Gly Glu Gly Pro Gly Pro Lys Pro Leu Ser Val Ala Gly Ala
            315                 320                 325 gat ccg tgaggaggaa gcccagggag gaggaggagg aggctgaggc caccttctg        1308
Asp Pro cagttaggcc tggaagggca cttctgagtg ccaggaaagg cagctttagt gcagacctag    1368
atcacagcta ctttcttgt ccctgtgggg tcttacagat gtgtctctga gtagtaaagg     1428
cttagccttg ttctgttttg ttgttttttg gaggggaagg ttagtcaggc ctgagtattc    1488
atgtaacatt ctaaaattgt gccagcgagc accgtgaacg actgcaatgc aagcgggtct    1548
tgctggctaa aatgcccagg taaagggttg gttggacaca gcgcttagtg cacgctgtca    1608
tcatggacat cataatcagt tgtgaaaaac acgcgaacct atgacacttc ttattccaca    1668
ctgaatgtga aattgcatgt tcagatgttt nactacgagg cctggctcac aggaagtgtt    1728
cagtaaaagt atgcactgtt agattactga taacgcggat agattttgt ttaccataaa     1788 ttgttccaga tttatattaa tggaaggaag tgtgcattta ttagctatta ctcaacttta    1848
caatgcaaac atcttatttc tcatctttaa acatgtcgac cagtttaatt gaaaagtatt    1908
ctgagactgc aaaatggggt gttaaaaaat actgcagtta cggagctgtg taaaccagtt    1968
tctcattgca taagatacag atgtaaattg catggagagg ttgatatgca cctgtacagt    2028
aattcactcc cccatttcac ttctttgtca gagaatagtt cttgttcata ctgagtgttc    2088
```
taaatttgaa gttatatata caaattaaaa tattttaaaa aaaaaaaaaa g    2139

<210> SEQ ID NO 4
<211> LENGTH: 329
<212> TYPE: PRT
<213> ORGANISM: homo sapiens

<400> SEQUENCE: 4

```
Met Ala Met Thr Leu Leu Glu Asp Trp Cys Arg Gly Met Asp Val Asn
1               5                   10                  15

Ser Gln Arg Thr Leu Leu Val Trp Gly Ile Pro Val Asn Cys Asp Glu
            20                  25                  30

Ala Glu Ile Glu Glu Thr Leu Gln Ala Ala Met Pro Gln Val Ser Tyr
        35                  40                  45

Arg Met Leu Gly Arg Met Phe Trp Arg Glu Glu Asn Ala Lys Ala Ala
    50                  55                  60

Leu Leu Glu Leu Thr Gly Ala Val Asp Tyr Ala Ala Ile Pro Arg Glu
65                  70                  75                  80

Met Pro Gly Lys Gly Val Trp Lys Val Leu Phe Lys Pro Pro Thr
                85                  90                  95

Ser Asp Ala Glu Phe Leu Glu Arg Leu His Leu Phe Leu Ala Arg Glu
            100                 105                 110

Gly Trp Thr Val Gln Asp Val Ala Arg Val Leu Gly Phe Gln Asn Pro
        115                 120                 125

Thr Pro Thr Pro Gly Pro Glu Met Pro Ala Glu Met Leu Asn Tyr Ile
130                 135                 140

Leu Asp Asn Val Ile Gln Pro Leu Val Glu Ser Ile Trp Tyr Lys Arg
145                 150                 155                 160

Leu Thr Leu Phe Ser Gly Lys Gly His Pro Arg Ala Trp Arg Gly Asn
                165                 170                 175

Phe Asp Pro Trp Leu Glu His Thr Asn Glu Val Leu Glu Glu Trp Gln
            180                 185                 190

Val Ser Asp Val Glu Lys Arg Arg Leu Met Glu Ser Leu Arg Gly
        195                 200                 205

Pro Ala Ala Asp Val Ile Arg Ile Leu Lys Ser Asn Asn Pro Ala Ile
    210                 215                 220

Thr Thr Ala Glu Cys Leu Lys Ala Leu Glu Gln Val Phe Gly Ser Val
225                 230                 235                 240

Glu Ser Ser Arg Asp Ala Gln Ile Lys Phe Leu Asn Thr Tyr Gln Asn
                245                 250                 255

Pro Gly Glu Lys Leu Ser Ala Tyr Val Ile Arg Leu Glu Pro Leu Leu
            260                 265                 270

Gln Lys Val Val Glu Lys Gly Ala Ile Asp Lys Asp Asn Val Asn Gln
        275                 280                 285

Ala Arg Leu Glu Gln Val Ile Ala Gly Ala Asn His Ser Gly Ala Ile
    290                 295                 300

Arg Arg Gln Leu Trp Leu Thr Gly Ala Gly Glu Gly Pro Gly Pro Lys
305                 310                 315                 320

Pro Leu Ser Val Ala Gly Ala Asp Pro
                325
```

<210> SEQ ID NO 5
<211> LENGTH: 18
<212> TYPE: DNA
<213> ORGANISM: homo sapiens

<400> SEQUENCE: 5
gggaatggcc gagacatc                                                       18

<210> SEQ ID NO 6
<211> LENGTH: 615
<212> TYPE: DNA
<213> ORGANISM: homo sapiens
<220> FEATURE:
<221> NAME/KEY: CDS
<222> LOCATION: (1)...(585)

<400> SEQUENCE: 6

| ccc | ctg | gca | ctg | tta | gag | gac | tgg | tgc | agg | ata | atg | agt | gtg | gat | gag |  48 |
|-----|-----|-----|-----|-----|-----|-----|-----|-----|-----|-----|-----|-----|-----|-----|-----|-----|
| Pro | Leu | Ala | Leu | Leu | Glu | Asp | Trp | Cys | Arg | Ile | Met | Ser | Val | Asp | Glu |     |
| 1   |     |     |     | 5   |     |     |     |     | 10  |     |     |     |     | 15  |     |     |

| cag | aag | tca | ctg | atg | gtt | acg | ggg | ata | ccg | gcg | gac | ttt | gag | gag | gct |  96 |
|-----|-----|-----|-----|-----|-----|-----|-----|-----|-----|-----|-----|-----|-----|-----|-----|-----|
| Gln | Lys | Ser | Leu | Met | Val | Thr | Gly | Ile | Pro | Ala | Asp | Phe | Glu | Glu | Ala |     |
|     |     |     |     | 20  |     |     |     |     | 25  |     |     |     |     | 30  |     |     |

| gag | att | cag | gag | gtc | ctt | cag | gag | act | tta | aag | tct | ctg | ggc | agg | tat | 144 |
|-----|-----|-----|-----|-----|-----|-----|-----|-----|-----|-----|-----|-----|-----|-----|-----|-----|
| Glu | Ile | Gln | Glu | Val | Leu | Gln | Glu | Thr | Leu | Lys | Ser | Leu | Gly | Arg | Tyr |     |
|     |     | 35  |     |     |     |     | 40  |     |     |     |     | 45  |     |     |     |     |

| aga | ctg | ctt | ggc | aag | ata | ttc | cgg | aag | cag | gag | aat | gcc | aat | gct | gtc | 192 |
|-----|-----|-----|-----|-----|-----|-----|-----|-----|-----|-----|-----|-----|-----|-----|-----|-----|
| Arg | Leu | Leu | Gly | Lys | Ile | Phe | Arg | Lys | Gln | Glu | Asn | Ala | Asn | Ala | Val |     |
|     | 50  |     |     |     |     | 55  |     |     |     |     | 60  |     |     |     |     |     |

| tta | cta | gag | ctt | ctg | gaa | gat | act | gat | gtc | tcg | gcc | att | ccc | agt | gag | 240 |
|-----|-----|-----|-----|-----|-----|-----|-----|-----|-----|-----|-----|-----|-----|-----|-----|-----|
| Leu | Leu | Glu | Leu | Leu | Glu | Asp | Thr | Asp | Val | Ser | Ala | Ile | Pro | Ser | Glu |     |
| 65  |     |     |     |     | 70  |     |     |     |     | 75  |     |     |     |     | 80  |     |

| gtc | cag | gga | aag | ggg | ggt | gtc | tgg | aaa | gtg | atc | ttt | aag | acc | cct | aat | 288 |
|-----|-----|-----|-----|-----|-----|-----|-----|-----|-----|-----|-----|-----|-----|-----|-----|-----|
| Val | Gln | Gly | Lys | Gly | Gly | Val | Trp | Lys | Val | Ile | Phe | Lys | Thr | Pro | Asn |     |
|     |     |     |     | 85  |     |     |     |     | 90  |     |     |     |     | 95  |     |     |

| cag | gac | act | gag | ttt | ctt | gaa | aga | ttg | aac | ctg | ttt | cta | gaa | aaa | gag | 336 |
|-----|-----|-----|-----|-----|-----|-----|-----|-----|-----|-----|-----|-----|-----|-----|-----|-----|
| Gln | Asp | Thr | Glu | Phe | Leu | Glu | Arg | Leu | Asn | Leu | Phe | Leu | Glu | Lys | Glu |     |
|     |     |     | 100 |     |     |     |     | 105 |     |     |     |     | 110 |     |     |     |

| ggg | cag | acg | gtc | tcg | ggt | atg | ttt | cga | gcc | ctg | ggg | cag | gag | gcg | ttg | 384 |
|-----|-----|-----|-----|-----|-----|-----|-----|-----|-----|-----|-----|-----|-----|-----|-----|-----|
| Gly | Gln | Thr | Val | Ser | Gly | Met | Phe | Arg | Ala | Leu | Gly | Gln | Glu | Ala | Leu |     |
|     |     | 115 |     |     |     |     | 120 |     |     |     |     | 125 |     |     |     |     |

| tct | cca | gcc | aca | gtg | ccc | tgc | atc | tca | cca | gaa | tta | ctg | gcc | cat | ttg | 432 |
|-----|-----|-----|-----|-----|-----|-----|-----|-----|-----|-----|-----|-----|-----|-----|-----|-----|
| Ser | Pro | Ala | Thr | Val | Pro | Cys | Ile | Ser | Pro | Glu | Leu | Leu | Ala | His | Leu |     |
|     | 130 |     |     |     |     | 135 |     |     |     |     | 140 |     |     |     |     |     |

| ttg | gga | cag | gca | atg | gca | cat | gcg | cct | cag | ccc | ctg | cta | ccc | atg | aga | 480 |
|-----|-----|-----|-----|-----|-----|-----|-----|-----|-----|-----|-----|-----|-----|-----|-----|-----|
| Leu | Gly | Gln | Ala | Met | Ala | His | Ala | Pro | Gln | Pro | Leu | Leu | Pro | Met | Arg |     |
| 145 |     |     |     |     | 150 |     |     |     |     | 155 |     |     |     |     | 160 |     |

| tac | cgg | aaa | ctg | cga | gta | ttc | tca | ggg | agt | gct | gtc | cca | gcc | cca | gag | 528 |
|-----|-----|-----|-----|-----|-----|-----|-----|-----|-----|-----|-----|-----|-----|-----|-----|-----|
| Tyr | Arg | Lys | Leu | Arg | Val | Phe | Ser | Gly | Ser | Ala | Val | Pro | Ala | Pro | Glu |     |
|     |     |     | 165 |     |     |     |     | 170 |     |     |     |     | 175 |     |     |     |

| gaa | gag | tcc | ttt | gag | gtc | tgg | ttg | gaa | cag | gcc | acg | gag | ata | gtc | aaa | 576 |
|-----|-----|-----|-----|-----|-----|-----|-----|-----|-----|-----|-----|-----|-----|-----|-----|-----|
| Glu | Glu | Ser | Phe | Glu | Val | Trp | Leu | Glu | Gln | Ala | Thr | Glu | Ile | Val | Lys |     |
|     |     |     | 180 |     |     |     |     | 185 |     |     |     |     | 190 |     |     |     |

| gag | tgg | cct | tgaacacaac caaaaaaaaa aaaaaaaag                            | 615 |
|-----|-----|-----|---------------------------------------------------------------|-----|
| Glu | Trp | Pro |                                                               |     |
|     |     | 195 |                                                               |     |

<210> SEQ ID NO 7
<211> LENGTH: 195
<212> TYPE: PRT
<213> ORGANISM: homo sapiens

<400> SEQUENCE: 7

Pro Leu Ala Leu Leu Glu Asp Trp Cys Arg Ile Met Ser Val Asp Glu
1               5                   10                  15

```
Gln Lys Ser Leu Met Val Thr Gly Ile Pro Ala Asp Phe Glu Glu Ala
             20                  25                  30

Glu Ile Gln Glu Val Leu Gln Glu Thr Leu Lys Ser Leu Gly Arg Tyr
         35                  40                  45

Arg Leu Leu Gly Lys Ile Phe Arg Lys Gln Glu Asn Ala Asn Ala Val
     50                  55                  60

Leu Leu Glu Leu Leu Glu Asp Thr Asp Val Ser Ala Ile Pro Ser Glu
 65                  70                  75                  80

Val Gln Gly Lys Gly Gly Val Trp Lys Val Ile Phe Lys Thr Pro Asn
                 85                  90                  95

Gln Asp Thr Glu Phe Leu Glu Arg Leu Asn Leu Phe Leu Glu Lys Glu
            100                 105                 110

Gly Gln Thr Val Ser Gly Met Phe Arg Ala Leu Gly Gln Glu Ala Leu
        115                 120                 125

Ser Pro Ala Thr Val Pro Cys Ile Ser Pro Glu Leu Leu Ala His Leu
    130                 135                 140

Leu Gly Gln Ala Met Ala His Ala Pro Gln Pro Leu Leu Pro Met Arg
145                 150                 155                 160

Tyr Arg Lys Leu Arg Val Phe Ser Gly Ser Ala Val Pro Ala Pro Glu
                165                 170                 175

Glu Glu Ser Phe Glu Val Trp Leu Glu Gln Ala Thr Glu Ile Val Lys
            180                 185                 190

Glu Trp Pro
        195

<210> SEQ ID NO 8
<211> LENGTH: 833
<212> TYPE: DNA
<213> ORGANISM: homo sapiens
<220> FEATURE:
<221> NAME/KEY: CDS
<222> LOCATION: (1)...(448)

<400> SEQUENCE: 8 gga cct cat gca cat agt gca ggc aga caa ccc gtc cat cag tgt aga        48
Gly Pro His Ala His Ser Ala Gly Arg Gln Pro Val His Gln Cys Arg
  1               5                  10                  15 aga gtg ttt gga ggc ctt taa gca agt gtt tgg gag cct aga gag ccg        96
Arg Val Phe Gly Gly Leu  *  Ala Ser Val Trp Glu Pro Arg Glu Pro
             20                  25                  30 cag gac agc cca ggt gag gta tct gaa gcc cta tca gga gga agg aga       144
Gln Asp Ser Pro Gly Glu Val Ser Glu Ala Leu Ser Gly Gly Arg Arg
         35                  40                  45 gaa ggt ctc agc cta tgt gtt acg gct aga aac cct gct ccg gag agc       192
Glu Gly Leu Ser Leu Cys Val Thr Ala Arg Asn Pro Ala Pro Glu Ser
     50                  55                  60 ggt gga gaa acg cgc cat ccc tcg gcg tat tgc gga cca ggt ccg cct       240
Gly Gly Glu Thr Arg His Pro Ser Ala Tyr Cys Gly Pro Gly Pro Pro
 65                  70                  75 gga gca ggt cat ggc tgg ggc cac tct taa cca gat gct gtg gtg ccg       288
Gly Ala Gly His Gly Trp Gly His Ser  *  Pro Asp Ala Val Val Pro
                 80                  85                  90 gct tag gga gct gaa gga tca ggg ccc gcc ccc cag ctt cct tga gct       336
Ala  *  Gly Ala Glu Gly Ser Gly Pro Ala Pro Gln Leu Pro  *  Ala
 95                 100                 105 aat gaa ggt aat acg gga aga aga gga gga aga ggc ctc ctt tga gaa       384
Asn Glu Gly Asn Thr Gly Arg Arg Gly Gly Arg Gly Leu Leu  *  Glu
            110                 115                 120
```

-continued

```
tga gag tat cga aga gcc aga gga acg aga tgg cta tgg ccg ctg gaa       432
 *  Glu Tyr Arg Arg Ala Arg Gly Thr Arg Trp Leu Trp Pro Leu Glu
         125                 130                 135 tca tga ggg aga cga c tgaaaaccac ctgggggcag gacccacagc cagtgggcta     488
Ser  *  Gly Arg Arg
             140 agacctttaa aaaattttttt tctttaatgt atgggactga aatcaaacca tgaaagccaa    548 ttattgacct tccttccttc cttccttccc tcccttcctc cttctctcct tctctccttt    608 ttttttttt tttttaaacc ctgttcttgg gtgggtgtgg gtataatact aagttgagat     668 gatatcattt acgggggaag gcgctttgtg aagtaggcct tatttctctt gtcctttcgt    728 acagggagga atttgaagta gatagaaacc gacctggatt actccggtct gaactcagat    788 cacgtaggac tttaatcgtt gaacaaacga acctttaata gcggg                     833
```

<210> SEQ ID NO 9
<211> LENGTH: 142
<212> TYPE: PRT
<213> ORGANISM: homo sapiens

<400> SEQUENCE: 9

```
Gly Pro His Ala His Ser Ala Gly Arg Gln Pro Val His Gln Cys Arg
 1               5                  10                  15

Arg Val Phe Gly Gly Leu Ala Ser Val Trp Glu Pro Arg Glu Pro Gln
             20                  25                  30

Asp Ser Pro Gly Glu Val Ser Glu Ala Leu Ser Gly Gly Arg Arg Glu
         35                  40                  45

Gly Leu Ser Leu Cys Val Thr Ala Arg Asn Pro Ala Pro Glu Ser Gly
     50                  55                  60

Gly Glu Thr Arg His Pro Ser Ala Tyr Cys Gly Pro Gly Pro Pro Gly
65                  70                  75                  80

Ala Gly His Gly Trp Gly His Ser Pro Asp Ala Val Pro Ala Gly
                 85                  90                  95

Ala Glu Gly Ser Gly Pro Ala Pro Gln Leu Pro Ala Asn Glu Gly Asn
            100                 105                 110

Thr Gly Arg Arg Gly Gly Arg Gly Leu Leu Glu Glu Tyr Arg Arg Ala
        115                 120                 125

Arg Gly Thr Arg Trp Leu Trp Pro Leu Glu Ser Gly Arg Arg
    130                 135                 140
```

<210> SEQ ID NO 10
<211> LENGTH: 1574
<212> TYPE: DNA
<213> ORGANISM: homo sapiens
<220> FEATURE:
<221> NAME/KEY: CDS
<222> LOCATION: (1)...(850)

<400> SEQUENCE: 10

```
ggt cca ggg aaa ggg ggg tgt ctg gaa ggt gat ctt taa gac ccc taa       48
Gly Pro Gly Lys Gly Gly Cys Leu Glu Gly Asp Leu  *  Asp Pro  *
 1               5                  10 tca gga cac tga gtt tct tga aag att gaa cct gtt tct aga aaa aga      96
Ser Gly His  *  Val Ser  *  Lys Ile Glu Pro Val Ser Arg Lys Arg
 15                  20                  25 ggg gca gac ggt ctc ggg tat gtt tcg agc cct ggg gca gga ggg cgt      144
Gly Ala Asp Gly Leu Gly Tyr Val Ser Ser Pro Gly Ala Gly Gly Arg
         30                  35                  40 gtc tcc agc cac agt gcc ctg cat ctc acc aga att act ggc cca ttt     192
```

-continued

```
Val Ser Ser His Ser Ala Leu His Leu Thr Arg Ile Thr Gly Pro Phe
 45                  50                  55                  60 gtt ggg aca ggc aat ggc aca tgc gcc tca gcc cct gct acc cat gag       240
Val Gly Thr Gly Asn Gly Thr Cys Ala Ser Ala Pro Ala Thr His Glu
             65                  70                  75 ata ccg gaa act gcg agt att ctc agg gag tgc tgt ccc agc ccc aga       288
Ile Pro Glu Thr Ala Ser Ile Leu Arg Glu Cys Cys Pro Ser Pro Arg
         80                  85                  90 gga aga gtc ctt tga ggt ctg gtt gga aca ggc cac gga gat agt caa       336
Gly Arg Val Leu  *  Gly Leu Val Gly Thr Gly His Gly Asp Ser Gln
             95                 100                 105 aga gtg gcc agt aac aga ggc aga aaa gaa aag gtg gct ggc gga aag       384
Arg Val Ala Ser Asn Arg Gly Arg Lys Glu Lys Val Ala Gly Gly Lys
        110                 115                 120 cct gcg ggg ccc tgc cct gga cct cat gca cat agt gca ggc aga caa       432
Pro Ala Gly Pro Cys Pro Gly Pro His Ala His Ser Ala Gly Arg Gln
    125                 130                 135 ccc gtc cat cag tgt aga aga gtg ttt gga ggc ctt taa gca agt gtt       480
Pro Val His Gln Cys Arg Arg Val Phe Gly Gly Leu  *  Ala Ser Val
140                 145                 150 tgg gag cct aga gag ccg cag gac agc cca ggt gag gta tct gaa gac       528
Trp Glu Pro Arg Glu Pro Gln Asp Ser Pro Gly Glu Val Ser Glu Asp
155                 160                 165                 170 cta tca gga gga agg aga gaa ggt ctc agc cta tgt gtt acg gct aga       576
Leu Ser Gly Gly Arg Arg Glu Gly Leu Ser Leu Cys Val Thr Ala Arg
                175                 180                 185 aac cct gct ccg gaa agc ggt gga gaa acg cgc cat ccc tcg gcg tat       624
Asn Pro Ala Pro Glu Ser Gly Gly Glu Thr Arg His Pro Ser Ala Tyr
            190                 195                 200 tgc gga cca ggt ccg cct gga gca ggt cat ggc tgg ggc cac tct taa       672
Cys Gly Pro Gly Pro Pro Gly Ala Gly His Gly Trp Gly His Ser  *
        205                 210                 215 cca gat gct gtg gtg ccg gct tag gga gct gaa gga tca ggg ccc gcc       720
Pro Asp Ala Val Val Pro Ala  *  Gly Ala Glu Gly Ser Gly Pro Ala
    220                 225                 230 ccc cag ctt cct tga gct aat gaa ggt aat acg gga aga aga gga gga       768
Pro Gln Leu Pro  *  Ala Asn Glu Gly Asn Thr Gly Arg Arg Gly Gly
235                 240                 245 aga ggc ctc ctt tga gaa tga gag tat cga aga gcc aga gga acg aga       816
Arg Gly Leu Leu  *  Glu  *  Glu Tyr Arg Arg Ala Arg Gly Thr Arg
            250                 255                 260 tgg cta tgg ccg ctg gaa tca tga ggg aga cga c tgaaaccac                860
Trp Leu Trp Pro Leu Glu Ser  *  Gly Arg Arg
                265                 270 ctgggggcag gacccacagc cagtgggcta agacctttaa aaatttttt tctttaatgt       920 atgggactga aatcaaacca tgaaagccaa ttattgacct tccttccttc cttcctttcc     980
ttcccttcct cctctctcc ttctctcctc ctctctcctc tcctctcctc tctttccttc     1040
cttccttcct tttttctttt tctctttctt ctttatttct tgggtctcac tctcatcacc    1100
caggctagag tgcagtggca caaaaatctc ggctcactgc agccttgact tcccaggctc    1160
aggctcaggt gatcctcaca ccttagcctc ccaagtacct gggactacag gcacgcacca    1220
ccatgcctag ctattctttt gtattttttgg tagagacagg gttttgctgt gttgctcagg   1280
ctggtctgga accctaggc tcaaatgatg tgcccaactc ggcctcccaa agtgctggga     1340
ttacaggcat gaaccgccat gcctggccct tgattttttct ttttaagaaa aaatatcta    1400 ggagtttctt agaccctatg tagattatta atgaacaaaa gattaaactc caaatattaa    1460
```

```
atagtaagcc tgaaggaatc tgaaacactt gtacttccaa ttttctttaa ataatcccaa   1520
atagaccaga attggcccat accatagaag aaagaattgg cagtcaaaaa aaaa        1574
```

<210> SEQ ID NO 11
<211> LENGTH: 271
<212> TYPE: PRT
<213> ORGANISM: homo sapiens

<400> SEQUENCE: 11

```
Gly Pro Gly Lys Gly Gly Cys Leu Glu Gly Asp Leu Asp Pro Ser Gly
 1               5                  10                  15

His Val Ser Lys Ile Glu Pro Val Ser Arg Lys Arg Gly Ala Asp Gly
             20                  25                  30

Leu Gly Tyr Val Ser Ser Pro Ala Gly Gly Arg Val Ser Ser His
         35                  40                  45

Ser Ala Leu His Leu Thr Arg Ile Thr Gly Pro Phe Val Gly Thr Gly
     50                  55                  60

Asn Gly Thr Cys Ala Ser Ala Pro Ala Thr His Glu Ile Pro Glu Thr
 65                  70                  75                  80

Ala Ser Ile Leu Arg Glu Cys Cys Pro Ser Pro Arg Gly Arg Val Leu
                 85                  90                  95

Gly Leu Val Gly Thr Gly His Gly Asp Ser Gln Arg Val Ala Ser Asn
            100                 105                 110

Arg Gly Arg Lys Glu Lys Val Ala Gly Gly Lys Pro Ala Gly Pro Cys
        115                 120                 125

Pro Gly Pro His Ala His Ser Ala Gly Arg Gln Pro Val His Gln Cys
    130                 135                 140

Arg Arg Val Phe Gly Gly Leu Ala Ser Val Trp Glu Pro Arg Glu Pro
145                 150                 155                 160

Gln Asp Ser Pro Gly Glu Val Ser Glu Asp Leu Ser Gly Gly Arg Arg
                165                 170                 175

Glu Gly Leu Ser Leu Cys Val Thr Ala Arg Asn Pro Ala Pro Glu Ser
            180                 185                 190

Gly Gly Glu Thr Arg His Pro Ser Ala Tyr Cys Gly Pro Gly Pro Pro
        195                 200                 205

Gly Ala Gly His Gly Trp Gly His Ser Pro Asp Ala Val Val Pro Ala
    210                 215                 220

Gly Ala Glu Gly Ser Gly Pro Ala Pro Gln Leu Pro Ala Asn Glu Gly
225                 230                 235                 240

Asn Thr Gly Arg Arg Gly Gly Arg Gly Leu Leu Glu Glu Tyr Arg Arg
                245                 250                 255

Ala Arg Gly Thr Arg Trp Leu Trp Pro Leu Glu Ser Gly Arg Arg
            260                 265                 270
```

<210> SEQ ID NO 12
<211> LENGTH: 2230
<212> TYPE: DNA
<213> ORGANISM: homo sapiens
<220> FEATURE:
<221> NAME/KEY: CDS
<222> LOCATION: (28)...(1416)
<221> NAME/KEY: misc_feature
<222> LOCATION: (1)...(2230)
<223> OTHER INFORMATION: n = A,T,C or G

<400> SEQUENCE: 12

```
ttcgaggaca tgccgttgac cttgtta cag gac tgg tgt cgg ggg gaa cac ctg    54
                      Gln Asp Trp Cys Arg Gly Glu His Leu
```

```
                    1                   5
aac acc cgg agg tgc atg ctc atc ctg ggg atc ccc gag gac tgt ggc    102
Asn Thr Arg Arg Cys Met Leu Ile Leu Gly Ile Pro Glu Asp Cys Gly
 10              15                  20                  25 gag gat gag ttt gag gag aca ctc cag gag gct tgc agg cac ctg ggc    150
Glu Asp Glu Phe Glu Glu Thr Leu Gln Glu Ala Cys Arg His Leu Gly
                 30                  35                  40 aga tac agg gtg att ggc agg atg ttt agg agg gag gag aac gcc cag    198
Arg Tyr Arg Val Ile Gly Arg Met Phe Arg Arg Glu Glu Asn Ala Gln
             45                  50                  55 gcg att cta ctg gag ctg gca caa gat atc gac tat gct ttg ctc cca    246
Ala Ile Leu Leu Glu Leu Ala Gln Asp Ile Asp Tyr Ala Leu Leu Pro
         60                  65                  70 agg gaa ata cca gga aag ggg ggg ccc tgg gaa gtg att gta aaa ccc    294
Arg Glu Ile Pro Gly Lys Gly Gly Pro Trp Glu Val Ile Val Lys Pro
     75                  80                  85 cgt aac tca gat ggg gaa ttt ctc aac aga ctg aac cgc ttc tta gag    342
Arg Asn Ser Asp Gly Glu Phe Leu Asn Arg Leu Asn Arg Phe Leu Glu
 90                  95                 100                 105 gag gag agg cgg acc gtg tca gat atg aac cga gtc ctc ggg tcg gac    390
Glu Glu Arg Arg Thr Val Ser Asp Met Asn Arg Val Leu Gly Ser Asp
                110                 115                 120 acc aat tgt tcg gct cca aga gtg act ata tca cca gag ttc tgg acc    438
Thr Asn Cys Ser Ala Pro Arg Val Thr Ile Ser Pro Glu Phe Trp Thr
            125                 130                 135 tgg gcc cag act ctg ggg gca gca gtg cag cct ctg cta gaa caa atg    486
Trp Ala Gln Thr Leu Gly Ala Ala Val Gln Pro Leu Leu Glu Gln Met
        140                 145                 150 ttg tac cga gaa cta aga gtg ttt tct ggg aac acc ata tcc atc cca    534
Leu Tyr Arg Glu Leu Arg Val Phe Ser Gly Asn Thr Ile Ser Ile Pro
    155                 160                 165 ggt gca ctg gcc ttt gat gcc tgg ctt gag cac acc act gag atg cta    582
Gly Ala Leu Ala Phe Asp Ala Trp Leu Glu His Thr Thr Glu Met Leu
170                 175                 180                 185 cag atg tgg cag gtg ccc gag ggg gaa aag agg cgg agg ctg atg gaa    630
Gln Met Trp Gln Val Pro Glu Gly Glu Lys Arg Arg Arg Leu Met Glu
                190                 195                 200 tgc tta cgg ggc cct gct ctc cag gtg gtc agt ggg ctc cgg gcc agc    678
Cys Leu Arg Gly Pro Ala Leu Gln Val Val Ser Gly Leu Arg Ala Ser
            205                 210                 215 aat gct tcc ata act gtg gag gag tgc ctg gct gcc ttg cag cag gtg    726
Asn Ala Ser Ile Thr Val Glu Glu Cys Leu Ala Ala Leu Gln Gln Val
        220                 225                 230 ttc gga cct gtg gag agc cat aaa att gcc cag gtg aag ttg tgt aaa    774
Phe Gly Pro Val Glu Ser His Lys Ile Ala Gln Val Lys Leu Cys Lys
    235                 240                 245 gcc tat cag gag gca gga gag aaa gta tct agc ttt gtg tta cgt ttg    822
Ala Tyr Gln Glu Ala Gly Glu Lys Val Ser Ser Phe Val Leu Arg Leu
250                 255                 260                 265 gaa ccc ctg ctc caa aga gct gta gaa aac aat gtg gta tca cgt aga    870
Glu Pro Leu Leu Gln Arg Ala Val Glu Asn Asn Val Val Ser Arg Arg
                270                 275                 280 aac gtg aat cag act cgc ctg aaa cga gtc tta agt ggg gcc acc ctt    918
Asn Val Asn Gln Thr Arg Leu Lys Arg Val Leu Ser Gly Ala Thr Leu
            285                 290                 295 cct gac aaa ctc cga gat aag ctt aag ctg atg aaa cag cga agg aag    966
Pro Asp Lys Leu Arg Asp Lys Leu Lys Leu Met Lys Gln Arg Arg Lys
        300                 305                 310 cct cct ggt ttc ctg gcc ctg gtg aag ctc ctg cgt gag gag gag gaa   1014
```

```
                                                                             -continued Pro Pro Gly Phe Leu Ala Leu Val Lys Leu Leu Arg Glu Glu Glu
    315                 320                 325 tgg gag gcc act tta ggt cca gat agg gag agt ctg gag ggg ctg gaa       1062
Trp Glu Ala Thr Leu Gly Pro Asp Arg Glu Ser Leu Glu Gly Leu Glu
330                 335                 340                 345 gta gcc cca agg cca cct gcc agg atc act ggg gtt ggg gca gta cct       1110
Val Ala Pro Arg Pro Pro Ala Arg Ile Thr Gly Val Gly Ala Val Pro
                350                 355                 360 ctc cct gcc tct ggc aac agt ttt gat gcg agg cct tcc cag ggc tac       1158
Leu Pro Ala Ser Gly Asn Ser Phe Asp Ala Arg Pro Ser Gln Gly Tyr
            365                 370                 375 cgg cgc cgg agg ggc aga ggc caa cac cga agg ggt ggt gtg gca agg       1206
Arg Arg Arg Arg Gly Arg Gly Gln His Arg Arg Gly Gly Val Ala Arg
        380                 385                 390 gct ggc tct cga ggc tca aga aaa cgg aaa cgc cac aca ttc tgc tat       1254
Ala Gly Ser Arg Gly Ser Arg Lys Arg Lys Arg His Thr Phe Cys Tyr
    395                 400                 405 agc tgt ggg gaa gac ggc cac atc agg gta cag tgc atc aac ccc tcc       1302
Ser Cys Gly Glu Asp Gly His Ile Arg Val Gln Cys Ile Asn Pro Ser
410                 415                 420                 425 aac ctg ctc ttg gta aag cag aag aaa cag gct gca gtt gag tcg gga       1350
Asn Leu Leu Leu Val Lys Gln Lys Lys Gln Ala Ala Val Glu Ser Gly
                430                 435                 440 aac ggg aac tgg gct tgg gac aag agc cat ccc aag tcc aag gcc aag       1398
Asn Gly Asn Trp Ala Trp Asp Lys Ser His Pro Lys Ser Lys Ala Lys
            445                 450                 455 tag gct cgg gag aac agg gcaacatttc ctaccacagc ccaaggagac              1446
 *  Ala Arg Glu Asn Arg
            460 aaaagagata ttgggaggag gggaaagaga agcccagaca acagcagat gagttgagtg      1506 gggcagaggg acagggcagc cagaccaagg ccaagcnttc tcaccccttng gccagttgga    1566 agggactttc agcaaccaag accacctggc aacaggctca gtggggtca ggtccaggtc     1626 cccgaagagg tgctggagag gaaagcaggg agccactgca tccagcacat ggggtgcctg    1686 ggcctcagat ggggacccca agaagcaga agctgaagaa ggtacggctg ggggttctgt     1746 cctgctcatc caaccacccc taaataccca ccctgtggac tttgagctga acatgcccac    1806 tggcccccag gccacatggg acctggagga gcctacctgg ggcctgcccc tgccagcagg    1866 tgccagggct ggtgaggaag agctgggggg cagaggtaaa gccctgcagg ggaggccaca    1926 gggtccatcc cgtcttcagg atcatctaca ctgcactagg ggagcccag gaaggcagca    1986 ccctggaggc cctgtgccag tgaggacagg agaccctaag gccccgggag cccagtgcca    2046 gccagaggtt gtgcaggcaa ggagaccaaa gattgatgag aagaccccca gcagggtac    2106 tgggtacccg gcaggccagt gccctcacag ttgacttgga ccagggtggc tgtgaaggga    2166 agtctttgtt gcaaggagg aggaaaaggg aggacttggt agggttttgt ttcttctgct    2226 tggg                                                                  2230

<210> SEQ ID NO 13
<211> LENGTH: 462
<212> TYPE: PRT
<213> ORGANISM: homo sapiens

<400> SEQUENCE: 13

Gln Asp Trp Cys Arg Gly Glu His Leu Asn Thr Arg Arg Cys Met Leu
1               5                   10                  15

Ile Leu Gly Ile Pro Glu Asp Cys Gly Glu Asp Glu Phe Glu Glu Thr
```

-continued

```
                20                  25                  30
Leu Gln Glu Ala Cys Arg His Leu Gly Arg Tyr Arg Val Ile Gly Arg
                35                  40                  45
Met Phe Arg Arg Glu Glu Asn Ala Gln Ala Ile Leu Glu Leu Ala
 50                  55                  60
Gln Asp Ile Asp Tyr Ala Leu Leu Pro Arg Glu Ile Pro Gly Lys Gly
 65                  70                  75                  80
Gly Pro Trp Glu Val Ile Val Lys Pro Arg Asn Ser Asp Gly Glu Phe
                85                  90                  95
Leu Asn Arg Leu Asn Arg Phe Leu Glu Glu Arg Arg Thr Val Ser
                100                 105                 110
Asp Met Asn Arg Val Leu Gly Ser Asp Thr Asn Cys Ser Ala Pro Arg
                115                 120                 125
Val Thr Ile Ser Pro Glu Phe Trp Thr Trp Ala Gln Thr Leu Gly Ala
 130                 135                 140
Ala Val Gln Pro Leu Leu Glu Gln Met Leu Tyr Arg Glu Leu Arg Val
 145                 150                 155                 160
Phe Ser Gly Asn Thr Ile Ser Ile Pro Gly Ala Leu Ala Phe Asp Ala
                165                 170                 175
Trp Leu Glu His Thr Thr Glu Met Leu Gln Met Trp Gln Val Pro Glu
                180                 185                 190
Gly Glu Lys Arg Arg Arg Leu Met Glu Cys Leu Arg Gly Pro Ala Leu
                195                 200                 205
Gln Val Val Ser Gly Leu Arg Ala Ser Asn Ala Ser Ile Thr Val Glu
 210                 215                 220
Glu Cys Leu Ala Ala Leu Gln Gln Val Phe Gly Pro Val Glu Ser His
 225                 230                 235                 240
Lys Ile Ala Gln Val Lys Leu Cys Lys Ala Tyr Gln Glu Ala Gly Glu
                245                 250                 255
Lys Val Ser Ser Phe Val Leu Arg Leu Glu Pro Leu Leu Gln Arg Ala
                260                 265                 270
Val Glu Asn Asn Val Val Ser Arg Arg Asn Val Asn Gln Thr Arg Leu
                275                 280                 285
Lys Arg Val Leu Ser Gly Ala Thr Leu Pro Asp Lys Leu Arg Asp Lys
 290                 295                 300
Leu Lys Leu Met Lys Gln Arg Arg Lys Pro Pro Gly Phe Leu Ala Leu
 305                 310                 315                 320
Val Lys Leu Leu Arg Glu Glu Glu Trp Glu Ala Thr Leu Gly Pro
                325                 330                 335
Asp Arg Glu Ser Leu Glu Gly Leu Glu Val Ala Pro Arg Pro Pro Ala
                340                 345                 350
Arg Ile Thr Gly Val Gly Ala Val Pro Leu Pro Ala Ser Gly Asn Ser
                355                 360                 365
Phe Asp Ala Arg Pro Ser Gln Gly Tyr Arg Arg Arg Gly Arg Gly
 370                 375                 380
Gln His Arg Arg Gly Gly Val Ala Arg Ala Ser Arg Gly Ser Arg
 385                 390                 395                 400
Lys Arg Lys Arg His Thr Phe Cys Tyr Ser Cys Gly Glu Asp Gly His
                405                 410                 415
Ile Arg Val Gln Cys Ile Asn Pro Ser Asn Leu Leu Leu Val Lys Gln
                420                 425                 430
Lys Lys Gln Ala Ala Val Glu Ser Gly Asn Gly Asn Trp Ala Trp Asp
 435                 440                 445
```

-continued

```
Lys Ser His Pro Lys Ser Lys Ala Lys Ala Arg Glu Asn Arg
    450                 455                 460

<210> SEQ ID NO 14
<211> LENGTH: 530
<212> TYPE: DNA
<213> ORGANISM: mus musculus

<400> SEQUENCE: 14
ctgcggtcgt tcttctgccc tcggcgggac gggcgcgggg agcccgggtc tctcctaaac      60
cccgcaaagg ctcccggacc tctgcgtgtt aaagagacga gcacgcacat cactgtaagc     120
ggcggcgcgg cggcgggcct ggtcgaatta gaatttaaat actctgagca ccatgacact     180
gagacttcta gaagactggt gcagagggat ggatatgaat cctcggaaag cactattggt     240
tgccggcatc cctccgacct gcggagtggc agacatagag gaggccctgc aggctggcct     300
tgctcccttg ggggaacaca gactgcttgg gaggatgttc aggagggatg agaacaagaa     360
tgtagccctg attgggctta cagtagagac tggcagtgcc tggtcccaa  ggaaatacct     420 gcaaaggag gtgtctggag agtgatcttt aagcctcctg atactgatag tgactttttg     480
tgcagattaa atgagttttt aaaggggag ggcatgacga tgggtgaatt               530
```